(12) United States Patent
Conklin et al.

(10) Patent No.: US 11,717,404 B2
(45) Date of Patent: Aug. 8, 2023

(54) PROSTHETIC MITRAL VALVE HOLDERS

(71) Applicant: Edwards Lifesciences Corporation, Irvine, CA (US)

(72) Inventors: Brian S. Conklin, Orange, CA (US); Derrick Johnson, Orange, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 396 days.

(21) Appl. No.: 16/936,364

(22) Filed: Jul. 22, 2020

(65) Prior Publication Data
US 2020/0345491 A1 Nov. 5, 2020

Related U.S. Application Data

(62) Division of application No. 15/796,147, filed on Oct. 27, 2017, now Pat. No. 10,722,356.
(Continued)

(51) Int. Cl.
*A61F 2/24* (2006.01)
*A61B 17/00* (2006.01)
*A61F 2/95* (2013.01)

(52) U.S. Cl.
CPC ...... *A61F 2/2427* (2013.01); *A61B 17/00234* (2013.01); *A61B 2017/00398* (2013.01);
(Continued)

(58) Field of Classification Search
CPC .. A61F 2/24; A61F 2/95; A61F 2/2427; A61F 2/2466; A61F 2/2418;
(Continued)

(56) References Cited

U.S. PATENT DOCUMENTS 3,656,185 A 4/1972 Carpentier
4,164,046 A 8/1979 Cooley
(Continued)

FOREIGN PATENT DOCUMENTS

CN 104523353 A 4/2015
EP 0338994 A1 10/1989
(Continued)

OTHER PUBLICATIONS

"Minimally Invasive Mitral Valve Surgery," Navia, Dept of Thoracic and CardioThoracic Surgery, The Cleveland Clinic Foundation, Cleveland, OH.
(Continued)

*Primary Examiner* — Vi X Nguyen
(74) *Attorney, Agent, or Firm* — Guy Cumberbatch

(57) ABSTRACT

Valve holders and introducers for delivering a prosthetic heart valve to an implant site are in various embodiments configured to facilitate insertion of prosthetic valves through small incisions or access sites on a patient's body. The valve holders can also be configured to reduce or eliminate the occurrence of suture looping or other damage to the prosthetic valve during implantation. A valve holder according to embodiments of the invention includes features that reduce or eliminate mistakes during implantation of the prosthetic valves, such as a removable activator dial and a removable handle that prevent implantation of the valve prior to proper deployment or adjustment of the holder. An introducer is provided which can facilitate passing of a prosthetic valve between adjacent ribs of a patient. Valve holders and introducers according to the various embodiments can be used in minimally invasive procedures, such as thoracotomy procedures.

19 Claims, 32 Drawing Sheets

Related U.S. Application Data

(60) Provisional application No. 62/417,207, filed on Nov. 3, 2016.

(52) U.S. Cl.
CPC ............ *A61B 2017/00407* (2013.01); *A61B 2017/00477* (2013.01); *A61F 2/2418* (2013.01); *A61F 2/9517* (2020.05)

(58) Field of Classification Search
CPC .................. A61F 2/2412; A61F 2/2436; A61F 2002/9517; A61B 17/00; A61B 17/00234; A61B 2017/00398
See application file for complete search history.

(56) References Cited

U.S. PATENT DOCUMENTS

| | | | |
|---|---|---|---|
| 4,217,665 A | 8/1980 | Bex et al. | |
| 4,602,911 A | 7/1986 | Ahmadi et al. | |
| 4,865,600 A | 9/1989 | Carpentier et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,258,021 A | 11/1993 | Duran | |
| 5,306,296 A | 4/1994 | Wright et al. | |
| 5,496,336 A | 3/1996 | Cosgrove et al. | |
| 5,593,435 A | 1/1997 | Carpentier et al. | |
| 5,607,471 A | 3/1997 | Seguin et al. | |
| 5,674,279 A | 10/1997 | Wright et al. | |
| 5,776,187 A | 7/1998 | Krueger et al. | |
| 5,776,189 A | 7/1998 | Khalid | |
| 5,824,066 A | 10/1998 | Gross | |
| 5,888,240 A | 3/1999 | Carpentier et al. | |
| 5,972,030 A | 10/1999 | Garrison et al. | |
| 6,102,945 A | 8/2000 | Campbell | |
| 6,143,024 A | 11/2000 | Campbell et al. | |
| 6,159,240 A | 12/2000 | Sparer et al. | |
| 6,183,512 B1 | 2/2001 | Howanec, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,250,308 B1 | 6/2001 | Cox | |
| 6,258,122 B1 | 7/2001 | Tweden et al. | |
| 6,319,280 B1 | 11/2001 | Schoon | |
| 6,332,893 B1 | 12/2001 | Mortier et al. | |
| 6,391,054 B2 | 5/2002 | Carpentier et al. | |
| 6,406,493 B1 | 6/2002 | Tu et al. | |
| 6,419,698 B1 | 7/2002 | Finger | |
| 6,602,288 B1 | 8/2003 | Cosgrove et al. | |
| 6,602,289 B1 | 8/2003 | Colvin et al. | |
| 6,619,291 B2 | 9/2003 | Hlavka et al. | |
| 6,709,456 B2 | 3/2004 | Langberg et al. | |
| 6,718,985 B2 | 4/2004 | Hlavka et al. | |
| 6,719,786 B2 | 4/2004 | Ryan et al. | |
| 6,726,717 B2 | 4/2004 | Alfieri et al. | |
| 6,764,510 B2 | 7/2004 | Vidlund et al. | |
| 6,797,002 B2 | 9/2004 | Spence et al. | |
| 6,800,090 B2 | 10/2004 | Alferness et al. | |
| 6,802,860 B2 | 10/2004 | Cosgrove et al. | |
| 6,805,710 B2 | 10/2004 | Bolling et al. | |
| 6,805,711 B2 | 10/2004 | Quijano et al. | |
| 6,858,039 B2 | 2/2005 | McCarthy | |
| 6,918,917 B1 | 7/2005 | Nguyen et al. | |
| 6,921,407 B2 | 7/2005 | Nguyen et al. | |
| 6,942,694 B2 | 9/2005 | Liddicoat et al. | |
| 6,955,689 B2 | 10/2005 | Ryan et al. | |
| 6,966,924 B2 | 11/2005 | Holmberg | |
| 6,986,775 B2 | 1/2006 | Morales et al. | |
| 7,101,395 B2 | 9/2006 | Tremulis et al. | |
| 7,118,595 B2 | 10/2006 | Ryan et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,294,148 B2 | 11/2007 | McCarthy | |
| 7,503,929 B2 | 3/2009 | Johnson et al. | |
| 7,691,143 B2 | 4/2010 | Wright et al. | |
| 8,152,844 B2 | 4/2012 | Rao et al. | |
| 8,460,173 B2 | 6/2013 | Schweich, Jr. et al. | |
| 8,986,376 B2 * | 3/2015 | Solem ................... | A61F 2/2409 623/2.37 |
| 9,333,076 B1 | 5/2016 | Edquist et al. | |
| D827,134 S | 8/2018 | Matsumura | |
| D846,122 S | 4/2019 | Pintor | |
| 2001/0010018 A1 | 7/2001 | Cosgrove et al. | |
| 2003/0033009 A1 | 2/2003 | Gabbay | |
| 2003/0040793 A1 | 2/2003 | Marquez | |
| 2004/0249452 A1 | 12/2004 | Adams et al. | |
| 2004/0249453 A1 | 12/2004 | Cartledge et al. | |
| 2005/0131533 A1 | 6/2005 | Alfieri et al. | |
| 2005/0182487 A1 | 8/2005 | McCarthy et al. | |
| 2005/0256567 A1 | 11/2005 | Lim et al. | |
| 2005/0256568 A1 | 11/2005 | Lim et al. | |
| 2005/0267572 A1 | 12/2005 | Schoon et al. | |
| 2005/0278022 A1 | 12/2005 | Lim | |
| 2006/0015178 A1 | 1/2006 | Moaddeb et al. | |
| 2006/0015179 A1 | 1/2006 | Bulman-Fleming et al. | |
| 2006/0020336 A1 | 1/2006 | Liddicoat | |
| 2006/0025858 A1 | 2/2006 | Alameddine | |
| 2006/0030885 A1 | 2/2006 | Hyde | |
| 2006/0241743 A1 | 10/2006 | Bergin et al. | |
| 2007/0162111 A1 | 7/2007 | Fukamachi et al. | |
| 2007/0179602 A1 | 8/2007 | Wright | |
| 2008/0071367 A1 * | 3/2008 | Bergin ................... | A61F 2/243 623/2.11 |
| 2009/0076599 A1 | 3/2009 | Bergin | |
| 2009/0192602 A1 | 7/2009 | Kuehn | |
| 2009/0192603 A1 | 7/2009 | Kuehn | |
| 2009/0192604 A1 | 7/2009 | Gloss | |
| 2009/0192606 A1 | 7/2009 | Gloss et al. | |
| 2009/0259305 A1 | 10/2009 | Lane et al. | |
| 2010/0030329 A1 | 2/2010 | Frater | |
| 2010/0191326 A1 | 7/2010 | Alkhatib | |
| 2011/0276128 A1 | 11/2011 | Cao et al. | |
| 2012/0136434 A1 | 5/2012 | Carpentier et al. | |
| 2016/0242903 A1 | 8/2016 | Edquist et al. | |
| 2020/0237510 A1 | 7/2020 | Carlino et al. | |

FOREIGN PATENT DOCUMENTS

| | | | |
|---|---|---|---|
| EP | 1034753 A1 | 9/2000 | |
| WO | 9302640 A1 | 2/1993 | |
| WO | 9814138 A1 | 4/1998 | |
| WO | 9949816 A1 | 10/1999 | |
| WO | 0108608 A1 | 2/2001 | |
| WO | 03020178 A1 | 3/2003 | |

OTHER PUBLICATIONS

Adams, David, et al., "Large Annuloplasty Rings Facilitate Mitral Valve Repair in Barlow's Disease," Society of Thoracic Surgeons 42.sup.ndAnnual Meeting, Jan. 30-Feb. 1, 2006.

Alonso-Lei, M.D., et al., Adjustable Annuloplasty for Tricuspid insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Brochure of "Cosgrove-Edwards Annuloplasty System," 2000.

Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

(56) References Cited

OTHER PUBLICATIONS

D.C. Miller, IMR Redux-To Repair or Replace?, Journal of Thoracic & Cardiovascular Surgery, pp. 1-8, 2001.
Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.
Gatti, et al., Preliminary Experience in Mitral Valve Repair Using the Cosgrove-Edwards Annuloplasty Ring, Interactive Cardiovascular and Thoracic Surgery, vol. 2(3), pp. 256-261,2003.
International Search Report from corresponding PCT Application No. PCT/US2009/043359 dated Aug. 4, 2009.
Melo, et al., Atrioventricular Valve Repair Using Externally Adjustable Flexible Rings: The Journal of Thoracic Cardiovascular Surgery, vol. 110, No. 5, 1995.
MGH Study Shows Mitral Valve Prolapse not a Stroke Risk Factor, Massachusetts General Hospital, pp. 1-3, Jun. 1999.
Salgo, et al., Effect of Annular Shape on Leaflet Curvature in Reducing Mitral Leaflet, American Heart Association, Circulation 200; pp. 106-711.
Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.
Smolens, et al., Mitral Valve Repair in Heart Failure, The European Journal of Heart Failure 2, pp. 365-371, 2000.
Watanabe, Nozomi, et al. "Mitral Annulus Flattens in Ischemic Mitral Regurgitation: Geometric Differences Between Inferior and Anterior Myocardial infarction: A Real-Time 3-Dimensional Echocardiographic Study," American Heart Association .COPYRGT. 2005; ISSN: 1524-4539.

\* cited by examiner

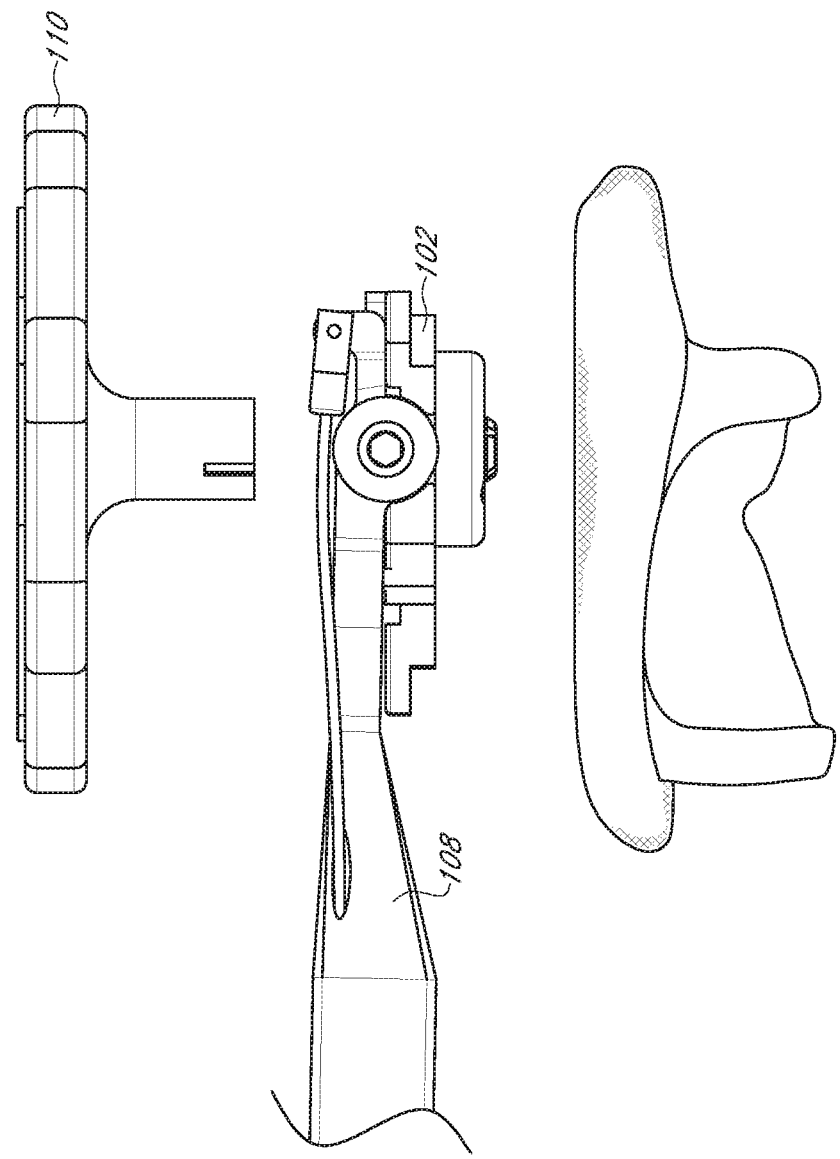

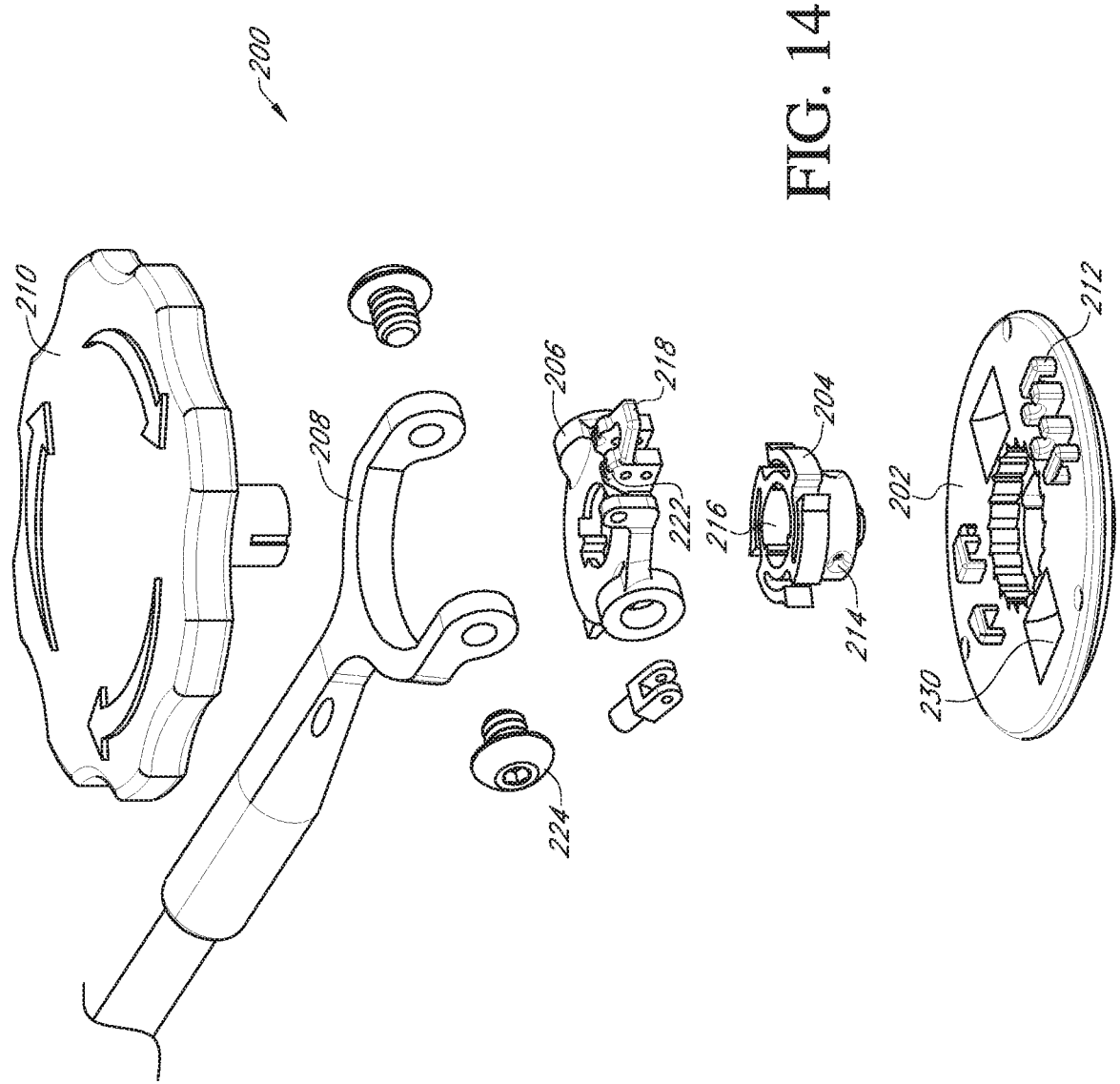

PROSTHETIC MITRAL VALVE HOLDERS

CROSS-REFERENCE TO RELATED APPLICATION

This application is a divisional of U.S. patent application Ser. No. 15/796,147, filed Oct. 27, 2017, which claims the benefit of U.S. Patent Application No. 62/417,207, filed Nov. 3, 2016, the entire disclosures of which are incorporated by reference for all purposes.

BACKGROUND

Field

The present disclosure generally concerns medical devices, deployment mechanisms, and methods for deploying such medical devices. More specifically, the disclosure relates to surgical replacement of native heart valves that have malformations and/or dysfunctions. The present disclosure also relates to prosthetic heart valves, and specifically, prosthetic mitral valves that can be implanted through a minimal sized incision. Embodiments of the invention relate to holders for facilitating the implantation of bioprosthetic replacement heart valves at native heart valves, for example, for a mitral valve replacement procedure. Embodiments of the invention also relate to methods of using the holders to facilitate implantation of prosthetic heart valves.

Description of Related Art

Referring first to FIG. 1, the human heart is generally separated into four pumping chambers, which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary arteries to the lungs to again supply the blood with oxygen.

Each of the valves associated with the chambers of the heart are one-way valves that have leaflets to control the directional flow of the blood through the heart and to prevent backflow of the blood into other chambers or blood vessels that are upstream of the particular chamber. For example, as described above, the mitral valve controls the flow of oxygenated blood from the left atrium to the left ventricle, while preventing blood flow back into the left atrium. The valves are each supported by an annulus having a dense fibrous ring attached either directly or indirectly to the atrial or ventricular muscle fibers. When a valve become diseased or damaged, leakage or regurgitation may occur, where some of the blood travels back upstream through the diseased or damaged valve, and the efficiency and/or general functionality of the heart may be compromised.

Various surgical techniques can be performed to repair or replace a diseased or damaged valve. In some valve replacement procedures, the leaflets of the diseased or damaged native valve are at least partially removed to prepare the valve annulus for receiving the prosthetic replacement valve. FIG. 2 shows an example of one type of popular prosthetic replacement valve 1 that is a tissue-type bioprosthetic valve generally constructed with natural-tissue valve leaflets 2, made for example, from porcine tissue or bovine pericardium, or from synthetic or semisynthetic material, that are mounted on a surrounding valve stent structure 3. The shape and structure of the leaflets 2 is supported by a number of commissure posts 4 positioned circumferentially around the valve stent structure 3. In these valves, a biocompatible cloth-covered suture or sewing ring 5 can also be provided on an inflow end of the stent structure 3 of the valve 1, to facilitate easier attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced to and properly positioned at the implant site. Additional sutures may also be applied between the prosthetic valve and the heart walls after proper placement, to securely attach or hold the valve implant in place. Meanwhile, in some cases, the prosthetic valves are implanted through small access channels using one of various minimally invasive surgical procedures, where visibility at the implant site may be impeded or obstructed. In addition, depending on the direction of implantation, for example, with some mitral valve replacement procedures, commissure posts of the stent or frame, or other portions, of the prosthetic valve may be pointed distally and advanced on a blind side of the valve, thereby obstructing visibility of the posts or other portions during advancement and implantation.

Each of the above factors may lead to tangling of the sutures with the valve prosthesis, most commonly with the commissure posts of the frame, since the commissure posts provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation. In some cases, such tangling may not be apparent to the practitioner at the time of implantation, and will only be revealed some time later when valve operation is observed to be improper or other complications arise in the patient, in which case, it may be necessary to initiate another procedure to repair or replace the prosthetic valve.

In addition, many existing bioprosthetic valves are not amenable to implantation through a minimal size incision, such as in thoracotomy procedures. Such procedures can require a surgical valve and its holder to fit through incisions of approximately 15-20 mm in its narrowest direction or dimension.

SUMMARY

Attempts have been made to resolve the issue of suture looping, some of which involve holders, which hold the prosthetic valves during delivery of the valves to the native valve annulus. In one example, a holder has a mechanism that urges the commissure posts of the prosthetic valve radially inwardly during delivery, such that the ends of the commissure posts are pointed inwards, to reduce the possibility of sutures catching against or looping around the commissure posts. After the valve prosthesis is delivered to the implant site, the holder is removed thereby releasing and expanding the commissure posts to their original positions. However, such holders may not be amenable to minimally invasive surgical techniques as the holder and valve combination may have a high or large profile, for example with the entire holder system positioned outside the valve, or the holder may not pull in the commissures enough to reduce the valve profile.

Meanwhile, Edwards Lifesciences has developed a valve holder system that can be used in mitral valve replacement procedures to protect the valve from suture looping during valve implantation. The system includes monofilament sutures that attach to both the holder and the commissures of the prosthetic valve, so that the sutures run over the outflow end of the valve between the ends of the commissures. When the holder is actuated, a central post extends distally through the prosthetic valve between the leaflets and pushes against the sutures that run across the middle of the valve between the commissures, pushing the sutures distally and causing an angled tent-like or "umbrella" effect on the sutures. The pressure on the sutures deflects the commissures slightly inwardly, while also forming angled surfaces or tracks with the sutures that slope outwardly from the central post to the commissure posts. These angled surfaces deflect any other sutures that might otherwise be looped over a commissure or leaflet away from the prosthetic valve. However, this system may not be very amenable to a minimally invasive surgical approach. The system does not pull in the commissures enough to reduce the valve profile, and the central post of the holder adds to the overall height of the valve once deployed, hindering minimally invasive surgical procedures.

In addition to the above, many of the newer holder designs also incorporate many additional parts that must be assembled by the practitioner or other end user, which may also lead to additional complications. Some holders incorporate various mechanisms and line connections, such that a number of additional steps must be taken by the practitioner to operate the holders correctly. Many of these holders have proven to be too complicated and/or prone to user error. For example, some holders may allow valves to be implanted without requiring that its mechanism be activated or deployed prior to delivery, for example, holders that allow delivery without deploying its mechanism to urge the commissure posts radially inward prior to insertion. Consequently, when practitioners use these holders improperly, suture looping still commonly occurs, while the implant process may also be further complicated by issues arising from user error. Further, some holders may require the practitioner to manually adjust the tightening of the holder to the prosthetic valves. Tightening too little can make the holder ineffective to prevent suture looping, while over-tightening can risk breaking one or more sutures of the system or damaging the valve.

Accordingly, a new replacement valve holder includes built-in mistake-proofing to ensure the anti-suture looping mechanism is engaged. In some embodiments, the new replacement valve holder can be designed to enable surgeons to implant the valve through minimal incisions, such as in thoracotomy procedures.

In one example, to fit through a minimal size incision, such as through an about 15-20 mm incision, a valve and holder combination can be collapsible in at least one direction. However, such holders and valves may not include a mechanism to actively collapse the valve into the reduced size configuration for delivery. Accordingly, an introducer according to other embodiments of the invention can be used with collapsible surgical valves and/or holders to introduce them into narrow surgical incisions, such as thoracotomies.

Features of the present disclosure provide for new holder systems and methods of using the holder systems, which reduce or eliminate the occurrence of suture looping or other damage to the prosthetic valves during implantation, for example, for mitral valve replacement using minimally invasive procedures or other procedures. Operation of the holders is also simplified, whereby the valves are prevented from being implanted prior to deployment of the holders, for example, via a removable activator dial, thereby reducing or eliminating mistakes caused by user error. According to embodiments, the dial cannot be removed until the system is activated, and while in place, the activator prevents the valve from being implanted. In some embodiments, the holder includes a removable handle that cannot be connected to the system until the removable activator dial is removed. The holders also provide for integrated alignment features or other safety features, such that over-deployment or under-deployment of the holders is prevented.

According to embodiments of the invention, holders for prosthetic valve delivery reduce or eliminate occurrences of suture looping and/or other damage to the valves when the valves are implanted, while the mechanisms for deploying these features are integrated into the holders in a way that reduces or eliminates mistakes in use and deployment.

In some embodiments, a mitral valve holder and handle system is provided that uses a ratchet mechanism to pull in the commissures of the valve towards the center of the valve, thereby eliminating the risk of suture looping. The holder has mistake-proofing features that prevent the physician from implanting the valve without engaging the system. In some embodiments, by flattening the profile of the valve, the holder system can allow implantation of the valve through a small or minimal incision. According to some embodiments, an introducer is provided to aid in implanting replacement valves through a minimal size incision, for example, by aiding in collapsing or otherwise reducing the profile of the valve and/or valve holder. The introducer can be used, for example, with mitral and/or aortic surgical valves. In some embodiments, such an introducer can be relatively short and only long enough to pass the valve past a patient's ribs. In other embodiments, the introducer can be relatively long and, for example, act as an atrial retractor, forming a channel all the way to the implant site in the case of a mitral valve.

BRIEF DESCRIPTION OF THE DRAWINGS

Further features and advantages of the invention will become apparent from the description of embodiments using the accompanying drawings. In the drawings:

FIG. 13A shows a side view of the valve holder of FIGS. 3 to 5 with a prosthetic valve in an unattached state;

FIG. 14 shows an exploded perspective view of a valve holder for a prosthetic mitral valve according to a second embodiment of the invention;

DETAILED DESCRIPTION

Disclosed herein are various tools, such as valve holders and introducers, for assisting in the delivery and implantation of prosthetic heart valves, such as mitral heart valves, at an implant site. Disclosed are also methods for preparing the prosthetic heart valves for such procedures. Embodiments of the valve holders reduce occurrences of various complications that may arise during implantation, while remaining simple for end users to use. By providing these improved valve holders, damage to the prosthetic valves during surgical procedures can be reduced, and additional costs for extended or additional procedures and/or replacement valves can be avoided.

The valve holders disclosed herein are particularly useful for avoiding suture looping and other valve damage during advancement of the prosthetic valves to the implant sites, as well as during final suturing of the valves at the native valve annulus. In many existing mitral valve replacement procedures, commissure posts of the prosthetic valve point distally away from practitioners, and in the direction of valve advancement and may be more prone to suture looping or other entangling. For such procedures, valve holders according to embodiments of the invention can urge the commissure posts radially inwards toward a center of the valve to reduce or eliminate suture looping. The presented embodiments can also include features that prevent valve implantation until the valve holders are in the activated or deployed positions. The holders can also include alignment features that prevent over-deployment or under-deployment. In this fashion, the holders provide ease of use while minimizing or reducing user errors.

The disclosed mitral valve holder and handle system is specifically designed to address shortcomings in previous valve holders. The disclosed system prevents clinicians from forgetting to deploy the system by means of a mistake-proof dial. The dial itself cannot be removed until the system is activated, and while the dial is in place, the dial prevents the valve from being implanted by: (1) physically making the system too bulky for implantation; (2) preventing the valve from being rotated or pivoted relative to the handle to a proper orientation for implantation; and (3) obstructing access to the sewing ring, thereby making placing sutures in the valve difficult.

Figure 1:
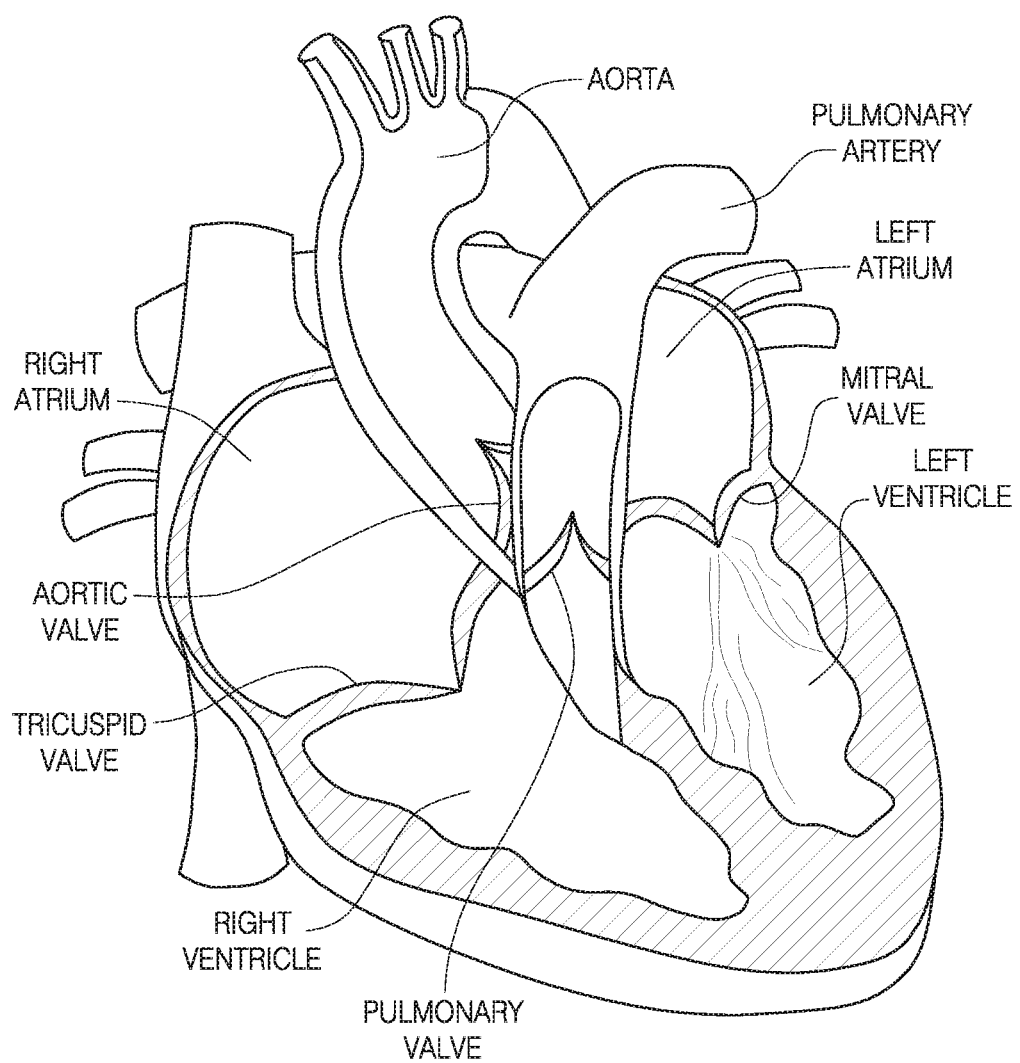
FIG. 1 shows a schematic cross-sectional view of a human heart.
Figure 2:
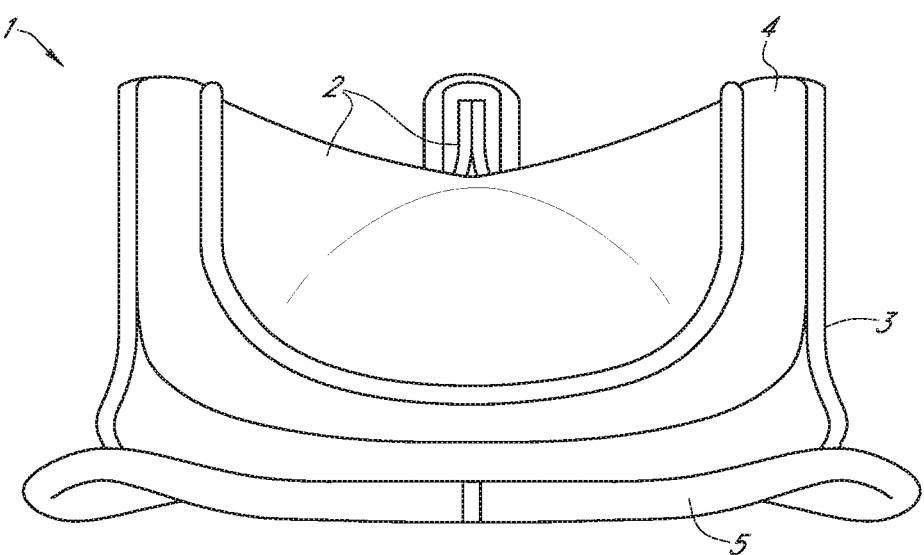
FIG. 2 shows a schematic perspective view of an example of a prosthetic valve that can be used with embodiments of the invention.
Figure 3:
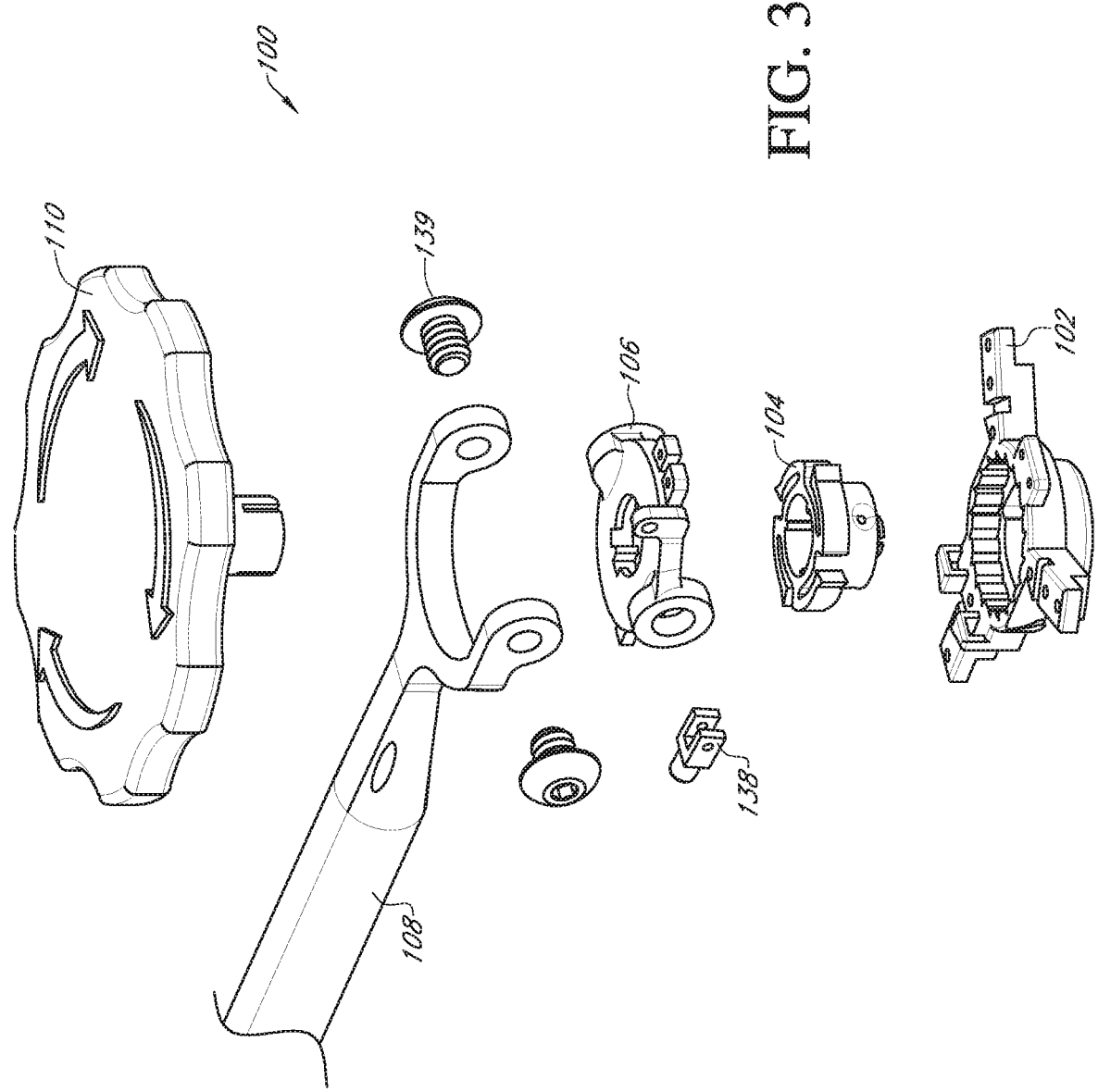
FIG. 3 shows an exploded perspective view of a valve holder for a prosthetic mitral valve according to a first embodiment of the invention.
Figure 4:
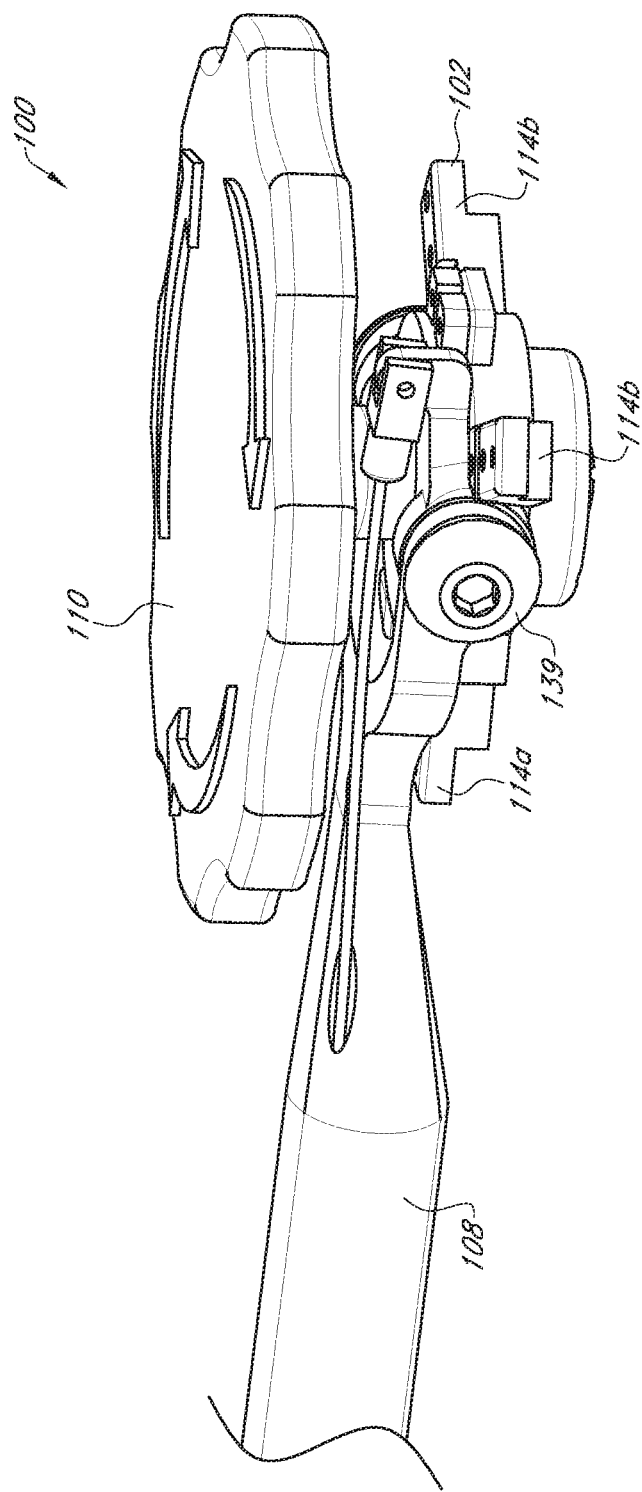
FIG. 4 shows a perspective view of the valve holder of FIG. 3 in an assembled state.
Figure 5:
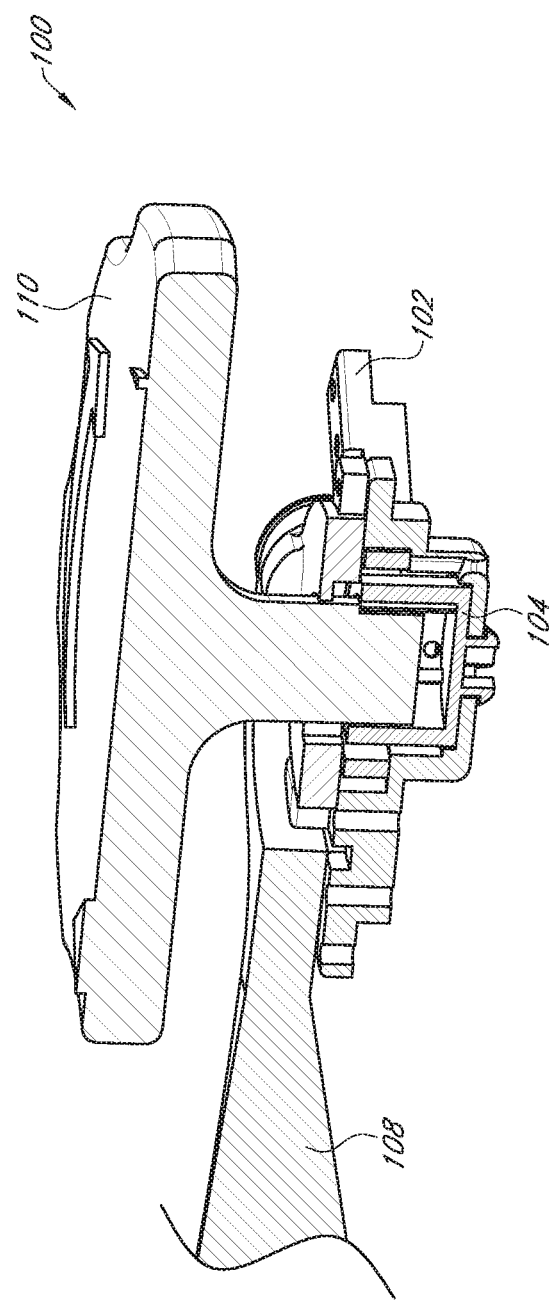
FIG. 5 shows a cross-sectional view of the valve holder of FIGS. 3 and 4.

FIGS. 3 to 5 show views of a valve holder 100 according to a first embodiment. FIG. 3 shows an exploded perspective view of the valve holder 100, FIG. 4 shows a perspective view of the valve holder 100 in an assembled state, and FIG. 5 shows a cross-sectional view of the valve holder 100 in the assembled state.

The valve holder 100 includes a body 102, a rotor 104, a swiveling delivery mount 106, a delivery handle 108, and an activator dial 110. As described in more detail below, a prosthetic heart valve can be attached to the body 102. The rotor 104 is positioned in a bore of the body 102 and is adjustable using the dial 110 to deploy or activate the valve holder 100 to adjust the prosthetic valve to a delivery position or configuration. The delivery mount 106, coupled to the delivery handle 108, is attached to the body 102 for delivering the valve to the implant site. The prosthetic valve can include a Nitinol wireform exhibiting a large amount of flexibility.

Figure 6A:
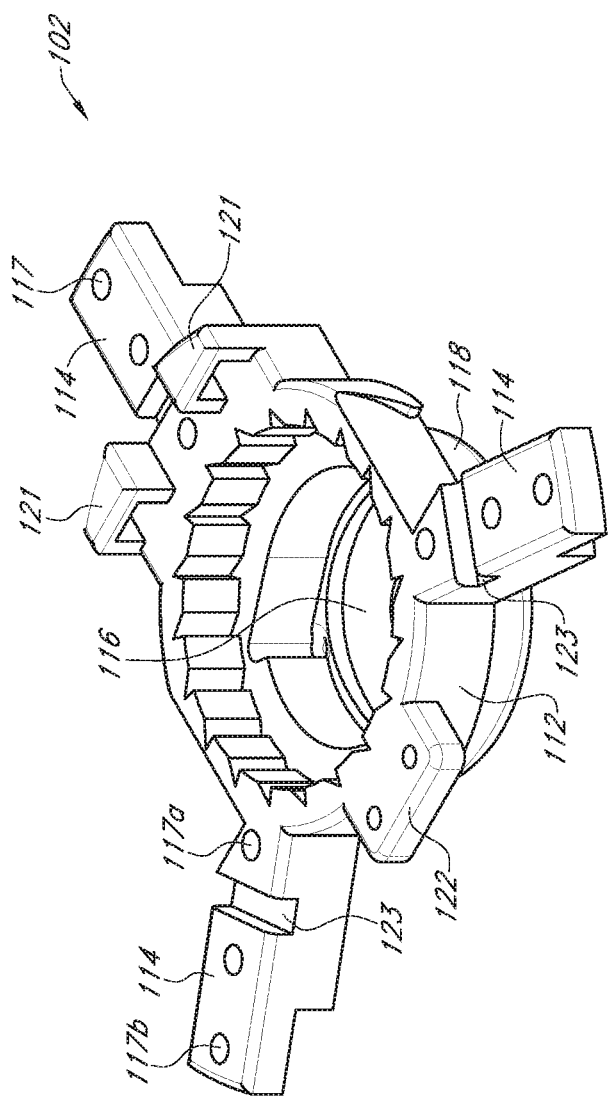
FIGS. 6A and 6B respectively show top and bottom views of a body of the valve holder of FIGS. 3 to 5.
Figure 6B:
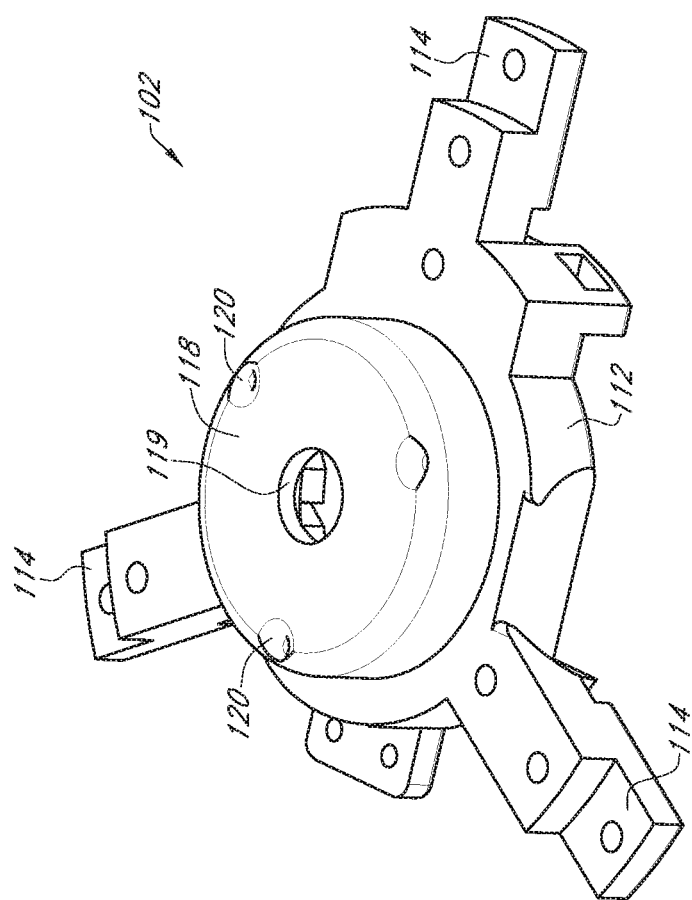

The body 102 of the valve holder 100 is shown in greater detail in FIGS. 6A and 6B. The body 102 includes a generally circular-shaped central hub 112 with a plurality of arms 114 extending from the central hub 112. The arms 114 serve as routing points for connecting commissure posts of the prosthetic valve to the valve holder 100 via sutures or other flexible material. In the embodiment shown, the body 102 includes three arms 114, but can include more or fewer arms 114 in other embodiments depending on the prosthetic valve the valve holder is intended to hold. The number of arms 114 generally corresponds to the number of commissure posts on the prosthetic valve. When three arms 114 are included in the body 102, the arms 114 can extend from the body 102 at approximately 120 degrees relative to each other.

Each of the arms 114 includes one or more through holes or bores 117 for routing the sutures. As will be described more fully below, the sutures are used to deploy or activate the valve holder 100 and place the valve in a delivery position where the commissure posts are urged radially inwards toward a center of the valve to reduce or eliminate suture looping. The through holes 117 extend transverse through the arms 114. The through holes 117 route the sutures across the top of the arms 114 to a region below the arms 114 where the sutures can connect to tips of the commissure posts, for example, by passing the sutures over and/or through other portions of the valve. Multiple through holes 117 can be provided. Through holes 117a, closer to the central hub 112, can be used to fasten or tie off an end of the sutures to the body 102, and to facilitate easier release of the valve from the valve holder 100. Through holes 117b, located nearer free ends of the arms 114, are used to route and position the sutures for connection to the commissure posts. In one embodiment, the sutures are routed through the arms 114 as follows. An end of the suture is fastened to the through hole 117a of the arms 114, for example, via a knot. The suture is then routed across a length of the arms 114 towards and through hole 117b. The free ends of the sutures are then in position to connect to the commissure posts of the valve. In other embodiments, a different number of through holes 117 can be provided, and in some embodiments, only one through hole 117 is provided on each arm 114. In addition, a surface of the arms 114 includes a recess or slot 123. The sutures extend across the recesses 123 when extended between holes 117a and 117b, such that there is a clearance underneath the sutures in the region of the recesses 123 to provide space for cutting the sutures. Cutting the sutures at the region of the recess 123 will release the valve from the valve holder 102. If the valve is in the delivery position, cutting the sutures will also allow the commissures to spring back to a normal or unbiased geometry by releasing the commissure posts. Each of the sutures connected to the arms 114 are cut to release the valve.

In order to have a good angle between the commissures of the valve, the sutures, and the holder 100 for transmitting force to pull in the commissures, the sutures are routed from the tip of a commissure to the opposite cusp area of the body 102.

In the body 102, a bore 116 is provided with an abutting surface 116a for receiving the rotor 104 therein. The abutting surface 116a serves as a stop for the rotor 104. The bore 116 extends into a bottom portion 118 of the body 102 that is circular-shaped and can have a smaller outer diameter than the central hub 112, for example, to provide clearance for a connected prosthetic valve. A through hole or bore 119 is positioned in the bottom portion 118 for coupling the rotor 104 to the body 102. The bottom portion 118 additionally includes through holes or bores 120 for routing the sutures from the tips of the commissure posts to inside of the bore 116 for attachment to the rotor 104. The number of through holes 120 generally corresponds to the number of arms 114. The through holes 120 can be co-linear with a direction of extension of the arms 114 and can be located along a periphery of the bottom portion 118. The through holes 120 can be located opposite to the position of the arms 114.

As shown in FIGS. 3 to 5, when the body 102 is connected to the delivery mount 106 and delivery handle 108, one of the arms 114a is aligned with the handle 108, for example co-linear with the handle 108, and two of the arms 114b extend away from the handle 108. In a region adjacent a base of the arm 114a, the central hub 112 includes upwardly extending projections 121. The projections 121 have a profile that matches an inner profile of the handle 108. On a side of the body 102 opposite to the arm 114a, a tab 122 is provided for connecting the delivery mount 106 to the body 102. Meanwhile, the arms 114b can be shaped to provide clearance for the delivery mount 106 and the delivery handle 108. Similarly, an outer surface of the central hub 112 in a region adjacent the arms 114b can also have cutouts or other surface features to provide clearance for the delivery mount 106 and the delivery handle 108.

While the central hub 112 and the bottom portion 118 are depicted as generally circular portions in the described embodiment, these portions can have different cross-sectional shapes in other embodiments.

Figure 7:
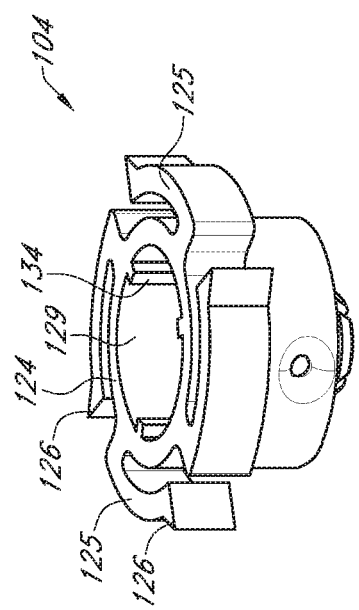
FIG. 7 shows a perspective view of a rotor of the valve holder of FIGS. 3 to 5.
Figure 8:
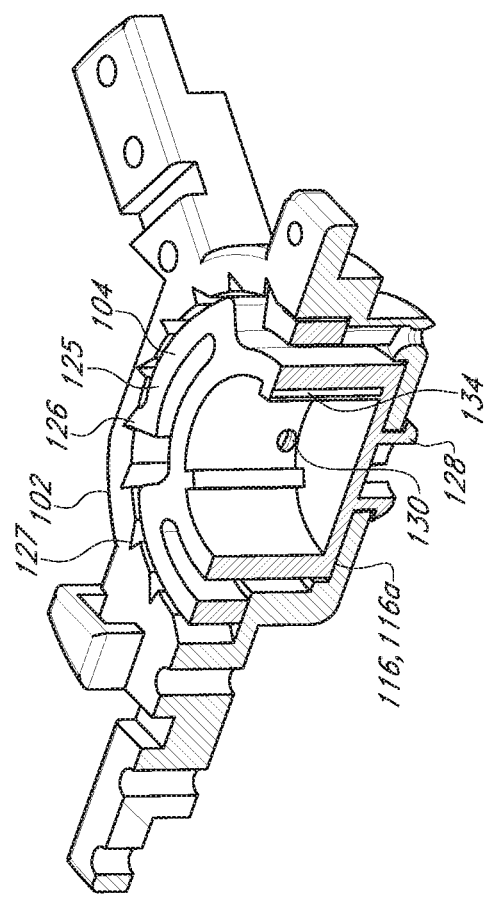
FIG. 8 shows a cross-sectional view of the rotor of FIG. 7 attached to the body of FIGS. 6A and 6B.

FIG. 7 shows a perspective view of the rotor 104 of the valve holder 100, and FIG. 8 shows a cross-sectional view of the rotor 104 attached to the body 102. The rotor 104 is configured to be positioned inside of the bore 116 of the body 102 and is rotatable with respect to the body 102. The rotor 104 is connectable to the sutures for adjusting the prosthetic valve to the delivery position using the activator dial 110, as described further below. The rotor 104 includes a central portion 124 with a longitudinal axis and a plurality of outwardly extending flexible arms 125. The flexible arms 125 are resilient such that the arms can be deflected inwards towards the central portion 124 and then released, causing the arms 125 to spring back into a relaxed shape when no longer deflected.

The rotor 104 is configured to be received in the bore 116 of the body 102. The rotor 104 includes a coupling mount 128 on the central portion 124 to rotatably couple to the hole 119 in the bottom portion 118 of the body 102. When coupled, the connection between the coupling mount 128 and the hole 119 permits rotation, but restricts translational movement of the rotor 104 relative to the body 102. The coupling mount 128 is depicted as a protrusion that extends to a position below the body 102, and may be snap fit into hole 119. The coupling mount in other embodiments can be designed in any number of different ways, so long as the connection permits rotation and restricts translation of the rotor 104 relative to the body 102. In some embodiments, the rotor 104 may be a monolithic part. In other embodiments, the rotor 104 may include separate components to connect to the body 102, such as snap rings, pins, and/or nuts or other fasteners. The separate components may be positioned inside the body 102, for example, placed in a slot in the bottom portion 118 of the body 102 (not illustrated). The separate components may additionally or alternatively be positioned outside of the body 102, for example, surrounding a portion of the coupling mount 128. Meanwhile, in other embodiments, the coupling mount 128 can, for example, have the form of a hole, which rotatably connects to a protrusion in the bottom portion 118 of the body 102. In other embodiments, the delivery mount 106 and/or the sutures secure the rotor within the body.

As shown in FIG. 8, end portions of the arms 125 have an engagement portion 126 in the form of teeth or pawls to engage a corresponding engagement portion 127 of an inner surface of the central hub 112, in the form of a plurality of notches or grooves. The teeth 126 of the rotor 104 engage the notches 127 of the body 102 to provide a one-way ratcheting mechanism that allows the rotor 104 to rotate in one direction relative to the body 102. The teeth 126 can have an asymmetric shape, such as a triangular shape, and the notches 127 can have a corresponding asymmetric cut out, such as a triangular cut-out, that permits the rotor 104 to rotate in only one direction relative to the orientation in FIG. 8 (e.g., clockwise as illustrated), but that prevents the rotor 104 from moving in a counter or opposite direction (e.g., counter-clockwise as illustrated). When the rotor 104 is rotated, the teeth 126 slide along an angular surface of the notches 127 such that the flexible arms 125 are compressed inwards and the teeth 126 disengage from their currently engaged notches 127. When the rotor 104 is rotated sufficiently that the teeth 126 approach subsequent notches 127, the resilient flexible arms 125 spring back into their original shape and engage the subsequent notches 127. Due to the shape of the teeth 126 and the notches 127, the rotor 104 is prevented from rotating in an opposite direction and back into the previously engaged notches 127. The one-way ratcheting mechanism provides ease of use and prevents misuse of the rotor during operation. Meanwhile, while the engagement portions 126, 127 in the disclosed embodiments are depicted as having a triangular shape, the engagement portions 126, 127 in other embodiments can be designed in any number of different ways, so long as the connections allow for one-way rotational movement or pivoting of the rotor 104 relative to the body 102. Further, in some embodiments, the engagement portions of the arms 125 of the rotor 104 can have the form of notches or grooves and the engagement portions of the body 102 can have the form of teeth or pawls with a shape that corresponds to the engagement portions of the arms.

Further, the rotor 104 includes a central opening 129 for connection to the activator dial 110, as described in more detail below. The rotor 104 additionally includes one or more holes 130 projecting through a sidewall of the rotor 104 and into the central opening 129. The holes 130 provide attachment points for connecting end regions of the sutures to the rotor 104. After the sutures are routed through holes 120 in the bottom portion 118 of the body 102 as described above, end portions of the sutures can be connected to the rotor 104 via the holes 130. When the sutures are connected to the rotor 104, rotation of the rotor 104 will create tension in the suture lines and further cause the sutures to be pulled in the direction of the moving rotor 104. Because the sutures are connected to the commissure posts of the prosthetic valve, this pulling force activates or deploys the valve holder 100 to adjust the prosthetic value to a collapsed or delivery position by transferring the force onto the commissure posts of the prosthetic valve. The commissure posts are thereby radially urged inwards toward a center of the prosthetic valve.

Figure 9:
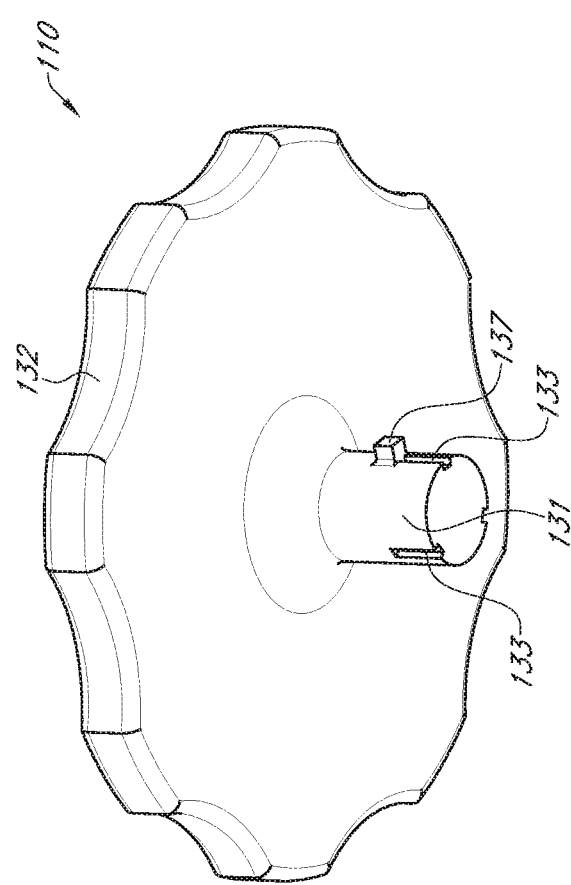
FIG. 9 shows a perspective view of an activator of the valve holder of FIGS. 3 to 5.

FIG. 9 shows a perspective view of the activator dial 110 of the valve holder 100. The dial 110 is used by an operator or user to rotate the rotor 104 and adjust the valve holder 100 to the deployed configuration. The activator dial 110 can be assembled with the valve holder 100 prior to use in a surgical procedure in an operating room. In one embodiment, for example, the activator dial 110 can be preassembled with the valve holder 100 during an assembly process by the manufacturer of the valve holder 100. Such an assembly step prior to use in surgical procedures can be done in order to aid in proper usage of the valve holder 100 and reduce the risk of inadvertent user errors.

The dial 110 includes a central shaft 131 having a central axis, and an enlarged gripping portion 132 extending therefrom. The central shaft 131 is sized and configured to be received in the central opening 129 of the rotor 104. The central shaft or stem 131 includes alignment keyways 133 in the shape of longitudinally extending slots or recesses for coupling to the rotor 104. The rotor 104 includes corresponding alignment keys 134 in the shape of longitudinally extending protrusions positioned inside the central opening 129 to mate to alignment keys 133 of the activator dial 110. The mating of the alignment features 133, 134 enables the rotor 104 to rotate together with the dial 110 when the gripping portion 132 of the activator dial 110 is turned. In various embodiments, the dial 110 can be turned either manually (for example, by the hands of an operator) or automatically via a motor or other means. Meanwhile, while three mating alignment features 133, 134 are respectively shown, the number of mating alignment features 133, 134 can be different in various embodiments. In one embodiment, for example, a single mating alignment feature 133, 134 can be used.

Figure 10:
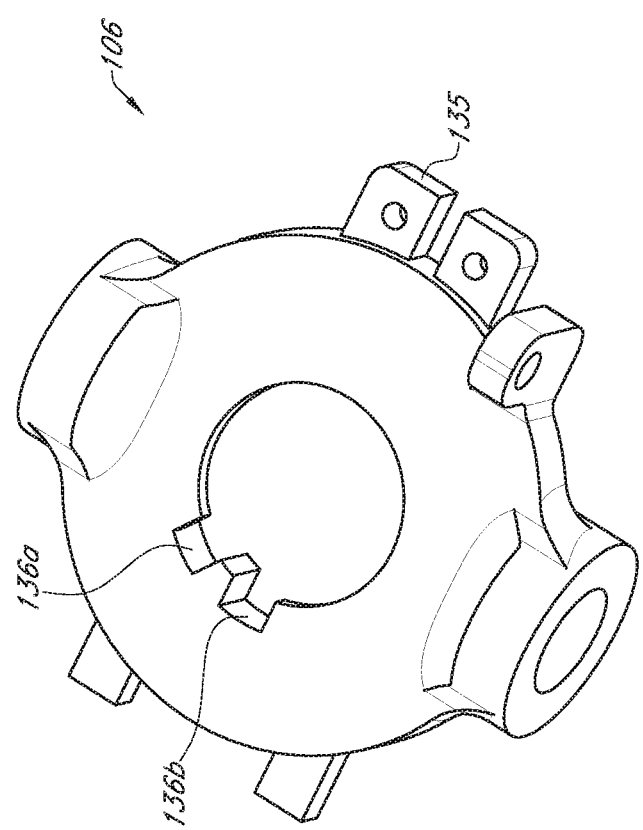
FIG. 10 shows a top view of a delivery mount of the valve holder of FIGS. 3 to 5.
Figure 11:
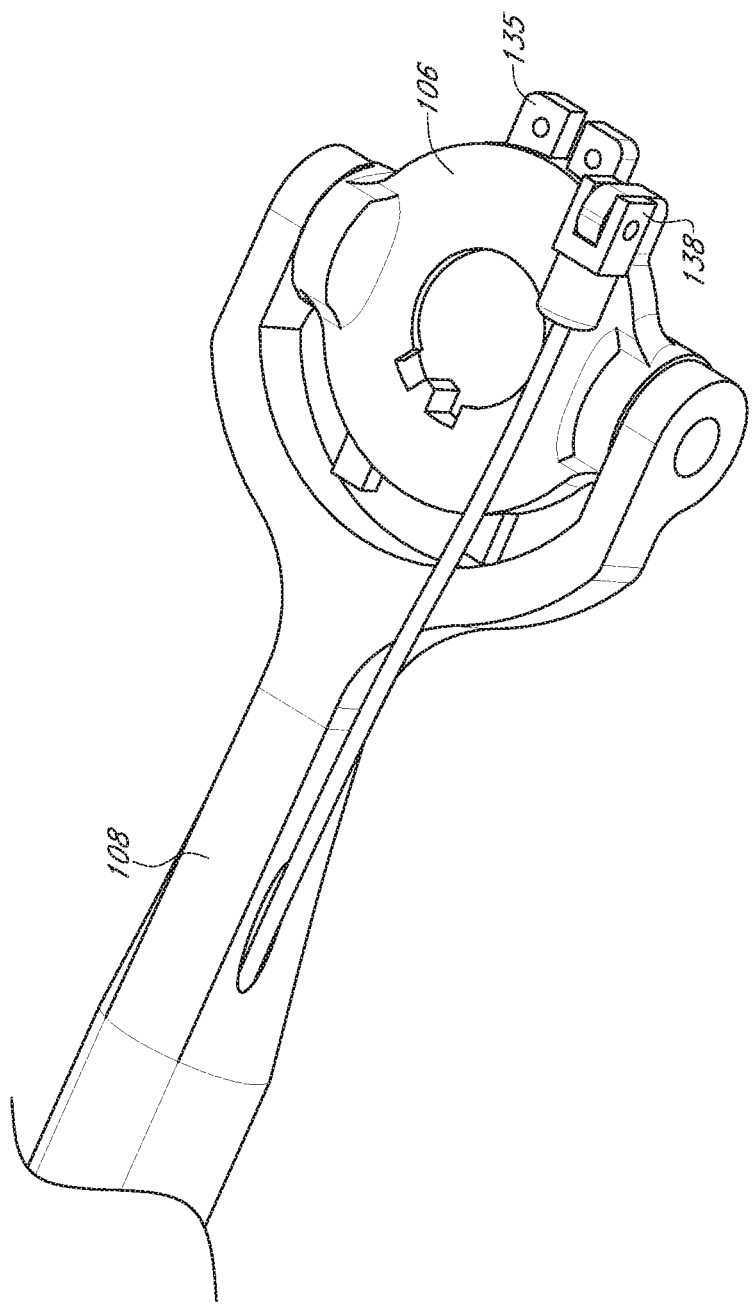
FIG. 11 shows a perspective view of the delivery mount of FIG. 10 attached to a handle.

FIGS. 10 to 11 show views of the delivery mount 106 and delivery handle 108 of the holder 100. The delivery mount 106 and handle 108 are used to deliver the valve to the implant site and place the valve into a proper configuration for implantation. The delivery mount 106 is configured to be positioned on an upper surface of the body 102 (e.g., against central hub 112) and has a generally circular shape that corresponds to the shape of the body 102. On an outer edge of the delivery mount 106 opposite to the handle 108, the delivery mount includes one or more tabs 135 configured to be aligned with tab 122 of the body 102. The tabs 122, 135 are used to connect the delivery mount 106 to the body 102 via a single suture or other connector. To connect the tabs 122, 135 by a single suture, the tabs 122, 135 can include aligned through holes or bores to route the suture. By using a single suture to connect the delivery mount 106 to the body 102, the delivery mount 106 and handle 108 can be quickly and easily removed from the body 102.

The delivery mount 106 and handle 108 are used to move the holder 100 between a first configuration for delivery to the implant site, and a second configuration for final implantation. In the first configuration, the handle 108 extends away from the body 102 in a direction opposite the tabs 122 (FIG. 6A), 135, such that the holder 100 and coupled valve have a low profile for insertion into the body. For example, in this first configuration, the holder 100 and coupled valve can have a slim cross-sectional profile that allows the assembly to be inserted past a patient's ribs. In the second configuration, the delivery mount 106, while coupled to the body 102, is rotated or swiveled relative to the handle 108 such that the handle 108 extends away from the prosthetic valve, for example in a direction that is substantially coaxial or parallel to a central axis of the prosthetic valve. In this second configuration, the prosthetic valve is in a configuration to be implanted in a heart of a human body (see, e.g., FIGS. 12 and 13D).

To rotate between the first and second configurations, the delivery mount 106 is rotatably coupled to the delivery handle 108 via fasteners 139 (FIG. 3). The delivery mount 106 can rotate relative to the handle 108 along an axis that extends between the fasteners 139. To swivel the delivery mount 106 relative to the handle 108, the holder 100 includes a pivoting connector or clevis 138 connected to an upper surface of the delivery mount 106 on a side opposite to the handle 108. The pivoting connector 138 is connected to one end of a flexible tension cable, and the other end of the flexible tension cable is connected to a slide or rotation mechanism located on a grip of the handle 108 (not shown). The rotation of the valve relative to the handle 108 can therefore be controlled with the slide located on the handle 108 grip. The slide or rotation mechanism may include a thumb wheel or a lever. The slide or rotation mechanism can be actuated to place tension onto the tension cable, thereby pulling or pushing the pivoting connector 138 and rotating the delivery mount 106 and the connected valve from the first configuration to the second configuration. Meanwhile, as shown in FIG. 4, when the activator dial 110 is connected to the valve holder 100, the dial 110 blocks the delivery mount 106 and handle 108 from entering into the second configuration. As such, the dial 110 acts as a stop that prevents the holder 100 from moving into the second configuration until the holder 100 has been deployed by the dial 110 to adjust the valve to the collapsed or delivery position and the dial 110 has been removed from the holder 100. Safety of procedures using the holder 100 is thereby enhanced, helping to reduce or eliminate misuse of the holder 100 during operation.

The delivery mount 106 additionally includes two alignment keyways 136a, 136b for use with the dial 110. The alignment keyways 136a, 136b provide ease of use and prevent misuse of the holder 100 during deployment. The alignment keyways 136a, 136b provide alignment for the activator dial 110 and act as stops that limit rotation of the dial 110 and the rotor 104 relative to body 102. To accomplish this, the alignment keyways 136a, 136b are sized and configured to receive a key or protrusion 137 (FIG. 9) of the activator dial 110 therethrough when the dial 110 is coupled to the rotor 104. More specifically, the key 137 is positioned on the central shaft or stem 131 of the activator dial 110 to interact with the keyways 136a, 136b of the mount 106. When positioning the central shaft 131 of the activator dial 110 in the central opening 129 of the rotor 104, the key 137 must be placed in keyway 136a in order to fully seat the activator dial 110 and to allow the activator dial 110 to rotate. In use, the rotor 104 can only be rotated in one direction, for example, the clockwise direction, as described above.

As described above, the activator dial 110 can be preassembled with the valve holder 100 prior to use in surgical procedures. To accomplish this, the central shaft 131 of the dial 110 is inserted into the rotor 104 with key 137 of the dial 110 inserted into keyway 136a of the delivery mount 106. The dial 110 and rotor 104 are then rotated relative to the body 102 such that teeth 126 and notches 127 become engaged, thus locking the dial 110 into the valve holder 100. In this configuration, the dial 110 is preassembled with the valve holder 100 for later use in surgical procedures. Because the engagement of the teeth 126 and notches 127 provide a one-way ratcheting mechanism, the activator dial 110 cannot be rotated counter-clockwise to be removed from through keyway 136. The engagement of the teeth 126 and notches 127 may be heard or felt by a "click" between the mating components as the rotor 104 is rotated. The teeth 126 and notches 127 can be identified as being engaged when the dial 110 and rotor 104 are rotated by at least one "click."

In use, the key 137 is inserted in keyway 136a, either before or during surgical procedures. Following insertion of the key 137 into keyway 136, the dial 110 can be rotated clockwise, during surgical procedures, until the key 137 is lined up with keyway 136b, at which point no further rotation is possible and the dial 110 can be removed. The key 137 and keyway 136b do not align until the dial 110 is rotated to the point of fully engaging the system. At the position of keyway 136b, the activator dial 110 cannot be rotated counter-clockwise by virtue of the one-way ratcheting mechanism of the rotor 104 and body 102. Further, when the key 137 is inserted in keyway 136a, the activator dial 110 also cannot be rotated in the counter-clockwise direction. Lastly, a portion of the delivery mount 106 between the keyways 136a, 136b can be slightly thickened to form an additional stop for the key 137 to prevent over-rotation of the dial 110. Accordingly, the keyways 136a, 136b limit the amount of rotation of the activator dial 110 to less than one full turn.

The keyways 136a, 136b enhance the safety of the holder 100 by eliminating over-tightening or under-tightening of the valve. Safety of procedures using the holder 100 is enhanced because the keyways 136, 136b can only be used in one way. Safety is also enhanced because the dial 110 can be preassembled with the holder 100 prior to use in surgical procedures. Meanwhile, once the dial 110 is assembled with the holder 100, the activator dial 110 can only be removed from the holder 100 when the key 137 reaches keyway 136b, requiring adjustment of the holder 100 into the second configuration before the dial can be removed.

When the activator dial 110 is removed, the holder 100 can have a low profile for implantation through minimally invasive incisions. In one embodiment, the height of the holder with an attached valve is between about 12-20 mm when the holder 100 is in a deployed position and the commissures of the valve are pulled down and radially inward. In some embodiments, the valve and holder combination may have a height of less than or equal to about 14 mm, so that the assembly would easily fit between most patient's ribs without spreading the ribs. This can be important, as spreading the ribs can result in more painful recovery for the patient. By comparison, the height of typical valves when deployed is about 27 mm or greater, not including the holder. In addition, a pivot point of the holder 100 to adjust the holder 100 into the second configuration may be only between about 0 to 2 mm above an inflow edge of the valve. In one embodiment, the pivot point may be only about 1.27 mm above the inflow edge of the valve. Further, most of the ratchet mechanism of the holder 100 sits within the boundaries of the valve itself.

A length of the handle 108 may be selected or optimized for use in minimally invasive procedures, such as thoracotomy procedures. The handle 108 may be made out of a malleable material, such as aluminum or Nitinol.

Figure 12:
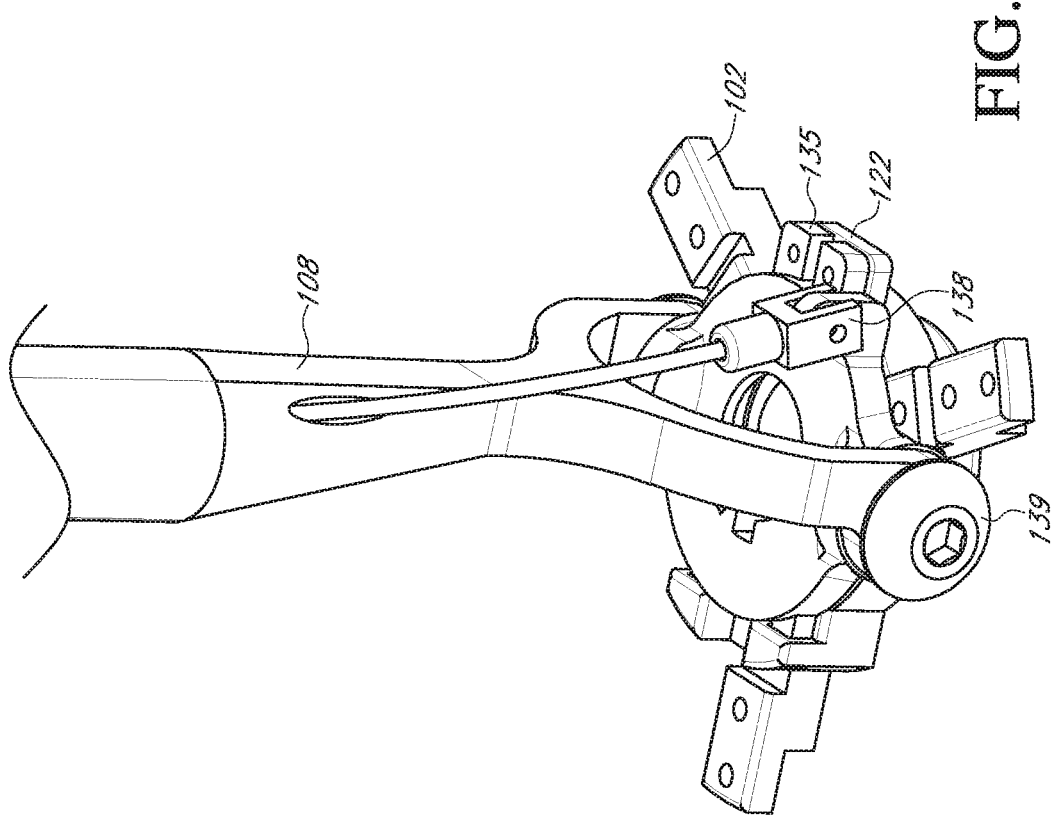
FIG. 12 shows a perspective view of the valve holder of FIGS. 3 to 5 in a deployed configuration with the activator removed and the delivery mount pivoted for insertion with sutures.

FIG. 12 shows a perspective view of the valve holder 100 with the delivery mount 106 in the second configuration. A single suture can connect the body 102 to the delivery mount 106 and handle 108 via the tabs 122, 135. Once the valve is parachuted or otherwise advanced to the native valve annulus, the handle 108 can be removed after cutting this single suture, which quickly releases the body 102 from the mount 106 and handle 108. The body 102 stays attached to the valve at this point, and the mechanism that pulls in the commissures remains activated.

Figure 13B:
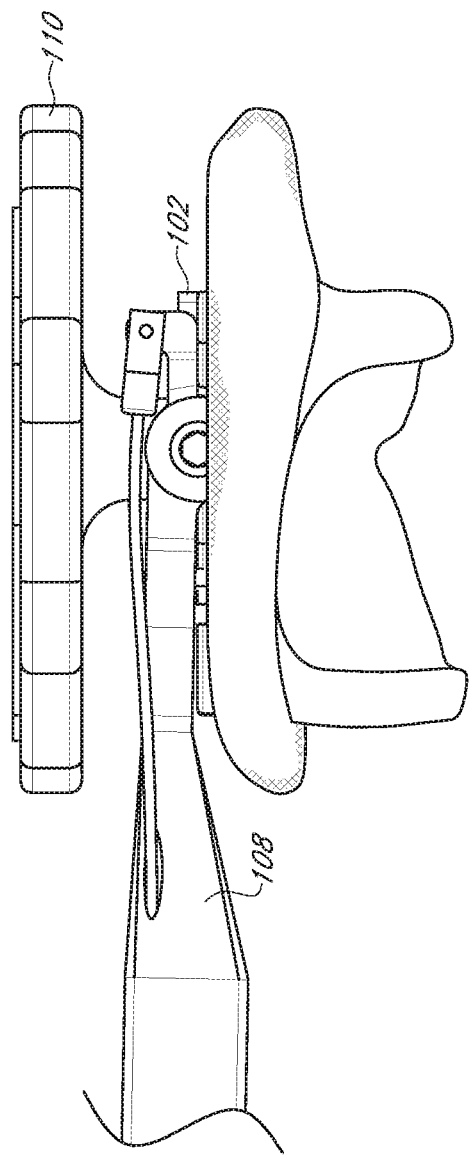
FIG. 13B shows a side view of the valve holder of FIGS. 3 to 5 in an un-deployed configuration with a replacement valve attached thereto.

FIGS. 13A to 13D show steps of using the holder 100 according to one embodiment. FIG. 13A shows a side view of the holder 100 and a prosthetic replacement valve to be implanted. The valve has not yet been coupled to the holder 100 and the activator dial 110 is also uncoupled from the holder 100. In this configuration, the valve can be attached to the holder 100 via three sutures that connect the commissure posts of the valve to the body 102 and the rotor 104. As described above, one end of each of the sutures is connected to respective arms 114 of the body 102 and passed through respective ones of the commissure posts. Opposite ends of each of the sutures are routed through respective holes 120 of the body 102 and holes 130 in the rotor 104. When initially connected, the holder 100 is in an undeployed state and the commissure posts of the valve are in an expanded or unbiased position, as shown in FIG. 13B.

In the state shown in FIG. 13B, the activator dial 110 is coupled to the holder 100 to adjust the configuration of the holder 100. To couple the dial 110 to the holder 100, the central shaft 131 of the activator dial 110 is placed inside the central opening 129 of the rotor 104 with key 137 of the dial 110 aligned and inserted through keyway 136a of the delivery mount 106. Proper use of the dial 110 is facilitated by the keyways 136a, 136b which minimize or prevent misuse of the holder 100. For example, the keyways 136a, 136b enable the dial 110 to be preassembled with the holder 100 prior to use in surgical procedures, as described above. In another example, should the dial 110 with the key 137 be aligned and inserted into keyway 136b, instead of keyway 136a, the activator dial 110 will not rotate due to the one-way ratcheting mechanism of the body 102 and the rotor 104.

Figure 13C:
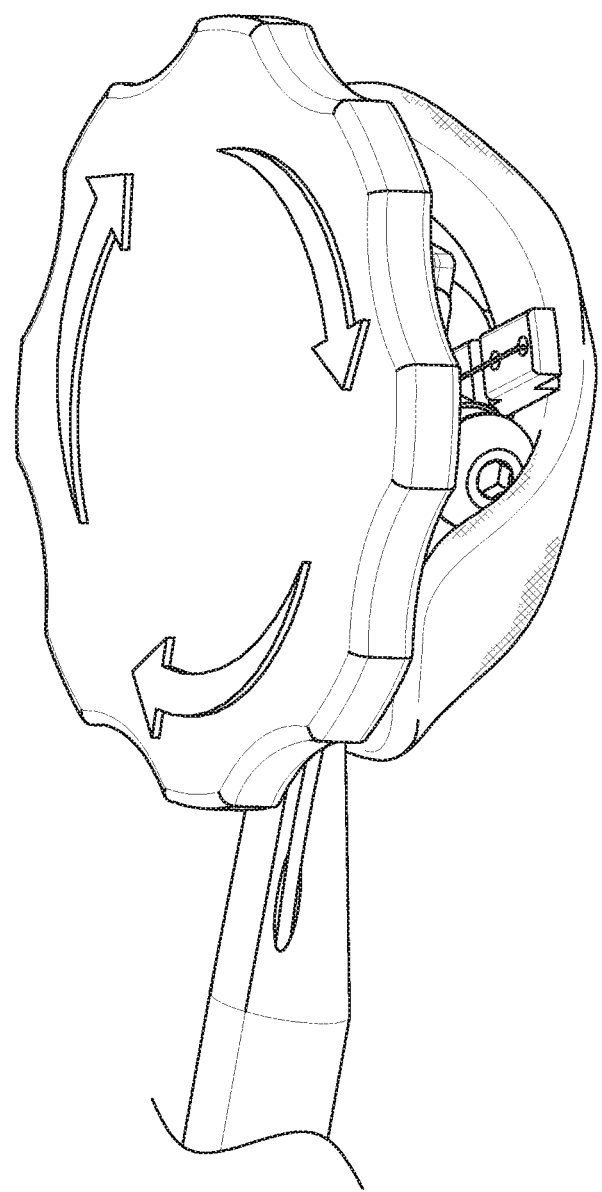
FIG. 13C shows a side view of the valve holder of FIGS. 3 to 5 in a deployed configuration with a replacement valve attached thereto.

From the configuration shown in FIG. 13B, the activator dial 110 can then be rotated in the clockwise direction, for example, for almost one full rotation until the key 137 is aligned with keyway 136b. As the activator dial 110 is rotated, the holder 100 is moved into a deployed state whereby the commissure posts of the valve are pulled down and inwards towards the center of the holder 100, as shown in FIG. 13C. In this state, the valve is ready for insertion into a body, but the activator dial 110 remains connected to the holder 100 and prevents insertion of the valve into a small or minimally invasive incision due to the dial's 110 large size. While the activator dial 110 is connected, the dial 110 also prevents the handle 108 from being rotated to move the holder 100 into the second configuration for final implantation.

From the configuration shown in FIG. 13C, the activator dial 110 can then be removed from the holder 100 when key 137 is aligned with keyway 136b. Once the activator dial 110 is removed, the low profile of the combined valve and holder 100 allow the assembly to be inserted into a patent and moved past a patient's ribs. Once past the patient's ribs, the slide or rotation mechanism on the handle 108 can be actuated to rotate or pivot the holder 100 from the first configuration to the second configuration.

Figure 13D:
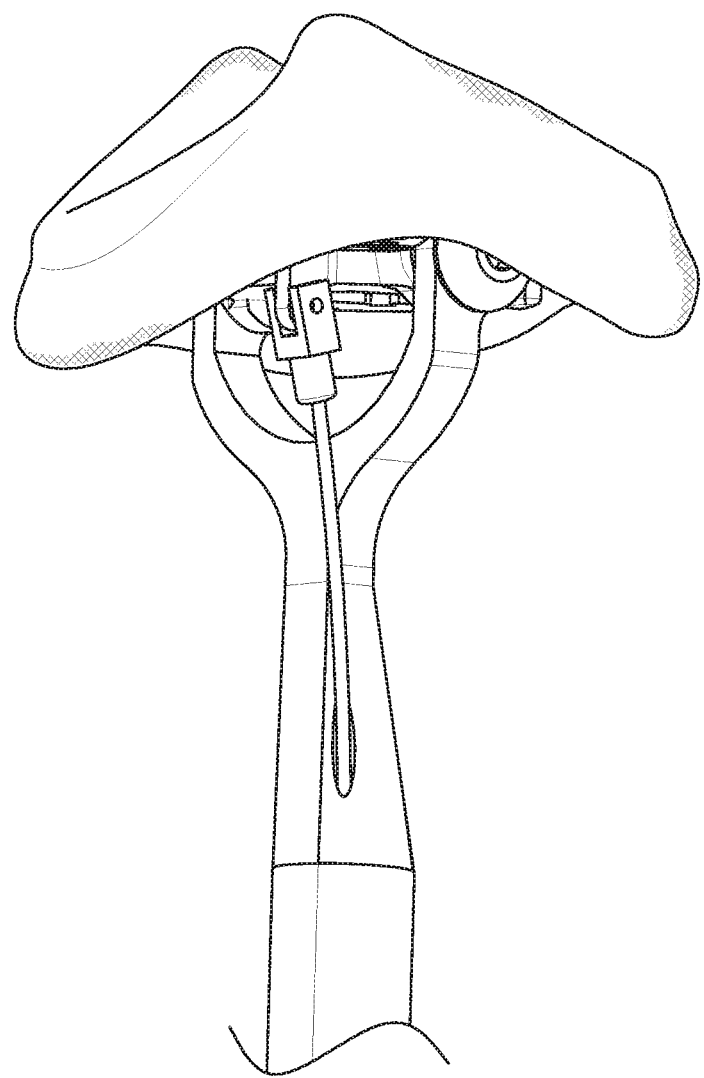
FIG. 13D shows a side view of the valve holder of FIGS. 3 to 5 in a deployed configuration with the activator removed and the delivery mount pivoted for insertion, and with a replacement valve attached thereto.

FIG. 13D shows the holder 100 in the second configuration, with an outflow end of the valve facing away from the handle 108. In this configuration, the assembly is in position and ready to be implanted at a native heart valve of a patient. In a later step during use of the holder 100, the operator can remove the delivery mount 106 and handle 108 from the holder 100 by cutting or untying the suture that connects tabs 122 and 135. In yet a later step during use of the holder 100, the operator can remove the valve from the holder 100 by cutting or untying the three sutures that connect to commissure posts to the holder 100. The three sutures may be cut in the region of the recesses 123 of the arms 114 of the body 102.

Figure 15:
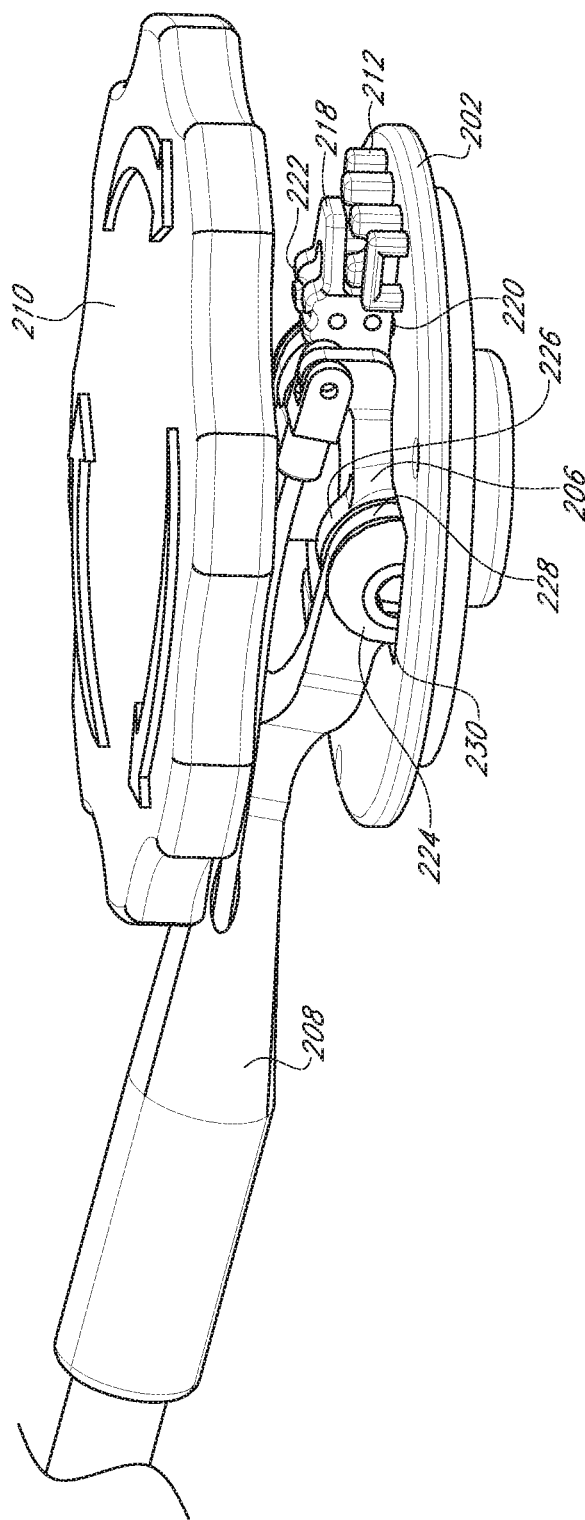
FIG. 15 shows a perspective view of the valve holder of FIG. 14 in an assembled state.
Figure 16:
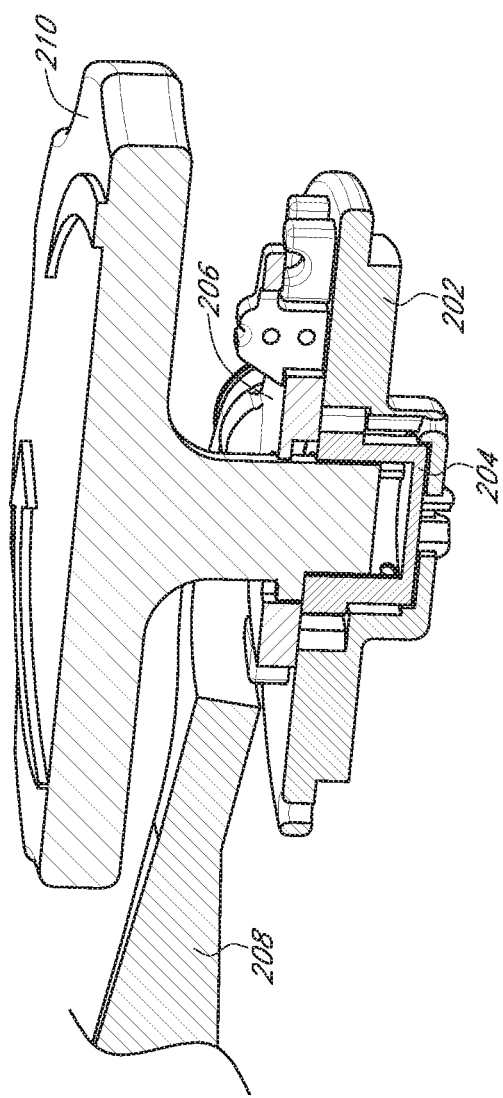
FIG. 16 shows a cross-sectional view of the valve holder of FIGS. 14 and 15.

FIGS. 14 to 16 show views of a valve holder 200 according to another embodiment. FIG. 14 shows an exploded perspective view of the valve holder 200, FIG. 15 shows a perspective view of the valve holder 200 in an assembled state, and FIG. 16 shows a cross-sectional view of the valve holder 200 in the assembled state. Similar to the first embodiment, the valve holder 200 of the second embodiment includes a body 202, a rotor 204, a delivery mount 206, a delivery handle 208, and an activator dial 210. The valve holder 200 of the second embodiment differs from the valve holder of the first embodiment in the design of the body 202, the delivery mount 206, and also in the connection of the valve to the body 102.

Figure 17:
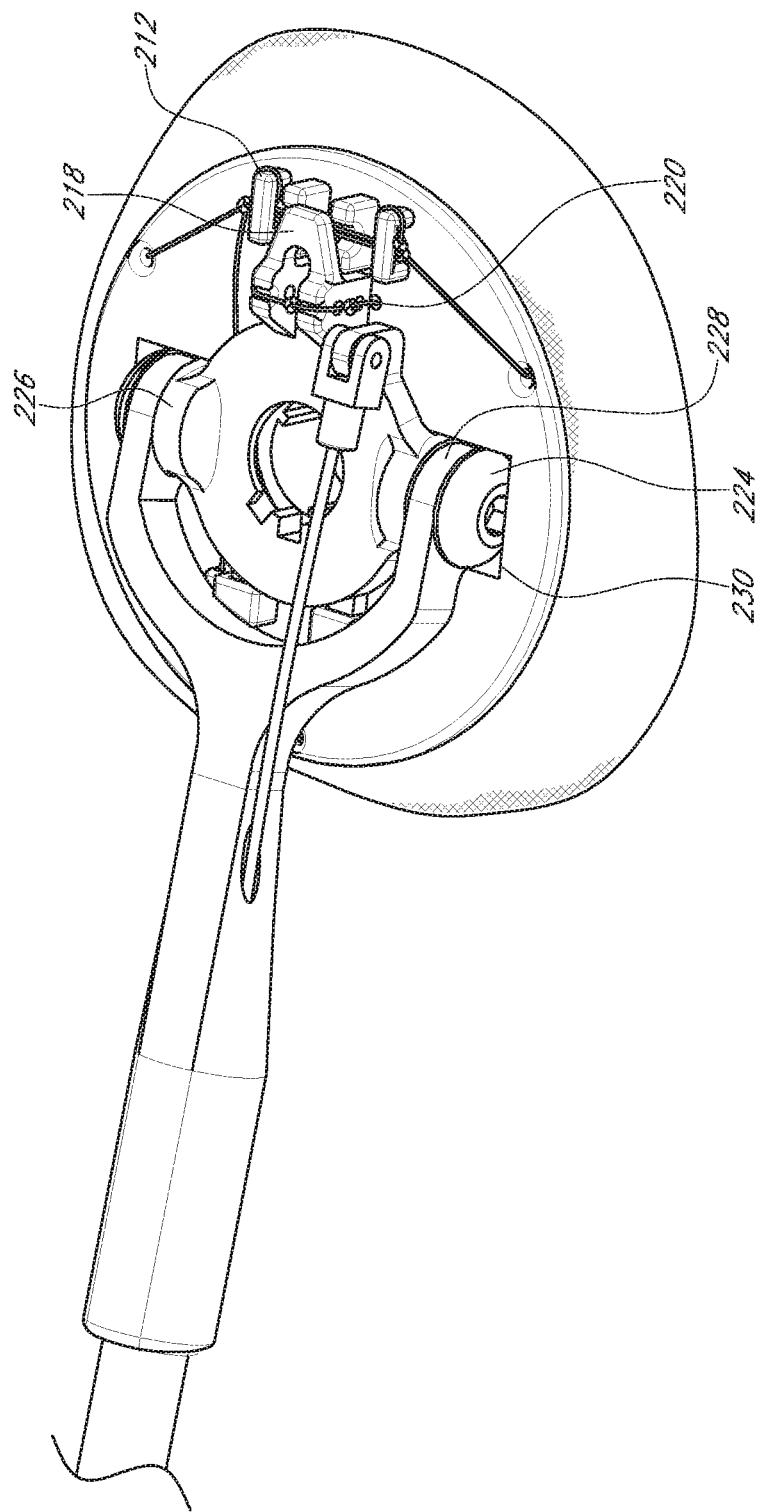
FIG. 17 shows a perspective view of the valve holder of FIGS. 14 to 16 in an assembled state with sutures.

The body 202 of this embodiment does not include the arms 114 of the first body, which were used for suture routing. Instead, the body 202 is shaped as a round or circular member with a suture mount 212 located at a periphery of the body 202 on a side opposite to the handle 208. The suture mount 212 is used as a single point to release the valve from the holder 200. For example, in embodiments where three sutures are used to attach to the commissure posts on the prosthetic valve (see FIG. 17), each of the sutures is routed through the suture mount 212. Similar to the first embodiment, the rotor 204 can be rotated by the activator dial 210 to deploy the prosthetic valve and cause the commissure posts to be urged down and radially inwards toward a center of the prosthetic valve.

In addition, in one embodiment, a single suture line can be used to connect the prosthetic valve to the holder 200 to simplify release of the valve. In such an embodiment, one end of the suture is connected to the rotor 204 via one or more holes 214 that extend through a sidewall of the rotor 204 and into a central opening 216 of the rotor 204. The suture is then routed from the hole 214, through a first commissure post, and then over the suture mount 212 of the body 202. The suture is then routed through a second commissure post and is again looped around the suture mount 212. Finally, the suture is routed through a third commissure post and again back to the suture mount 212, and is then tied off at the suture mount 212. When finished, the single suture connects all three commissure posts to the suture mount 212 and also to the rotor 204.

Meanwhile, the delivery mount 206 of the second embodiment differs from the first embodiment by the inclusion of a guard 218. The guard 218 is located at a periphery of the delivery mount 206 at a side opposite to the handle 208. The guard 218 is used to connect the delivery mount 206 to the body 202. The body 202 includes two through holes 220 (FIG. 15) that extend vertically through the body 202. When the body 202 and delivery mount 206 are connected, the through holes 220 of the body 202 are adjacent to the guard 218. A single suture can be used to connect the body 202 to the delivery mount 206 via holes 220 and the guard 218. To that end, the guard 218 includes notches 222 for ease of routing the single suture. This suture can be cut or untied to quickly release the body 202 from the mount 206 and handle 208.

Further, the guard 218 provides an additional safety feature against inadvertent or premature release of the valve from the holder 200. When the delivery mount 206 is coupled to the holder 200, the guard 218 is aligned with the suture mount 212 of the body 202, and is positioned over an upper surface of the suture mount 212 to cover the suture mount 212. The guard 218 blocks access to the suture connecting the valve to the holder 200, to prevent or make difficult any inadvertent or unintended cutting or breaking of the suture that would cause the holder 200 to be released from the valve while the delivery mount 206 remains coupled to the holder 200. Therefore, while the delivery mount 206 is connected to the body 202, a connected valve is restricted from being prematurely or inadvertently removed. When the delivery mount 206 is removed, the suture mount 212 is revealed and the suture can then be cut or untied to release the valve.

Assembly of the holder 200 according to one embodiment is as follows. First, the rotor 204 is received in the body 202 similar to the first embodiment. Next, one or more sutures are used to connect the holder 200 to the prosthetic valve. One end of the one or more sutures is connected to the rotor 204, and may be connected to a hole 214 extending through the sidewall of the rotor 204, as described above. The other end of the one or more sutures is routed through the commissure posts of the valve and connected to the suture mount 212 of the body 202. Next, the delivery mount 206 and handle 208 are coupled to the body 202. The delivery mount 206 is connected to the body 202 on a side opposite to the valve. The delivery mount 206 is positioned such that fasteners 224 and portions 226, 228 of the delivery mount 206 and handle 208, respectively, are received in slots 230 in the body 202. The delivery mount 206 is then coupled to the body 202 using one or more sutures via holes 220 in the body and the guard 218. When all of the described features are assembled, the valve is in position to be deployed using the activator dial 210, similarly as discussed with respect to the first embodiment. Additionally, once the activator dial 210 is removed, a slide or rotation mechanism on the handle 208 can be actuated to rotate the valve from a first configuration for insertion into a patient and into a second configuration for final implantation, also similarly as described with respect to the first embodiment. In other embodiments, the assembly sequence can be varied to achieve the same or similar assembled combinations.

Figure 18A:
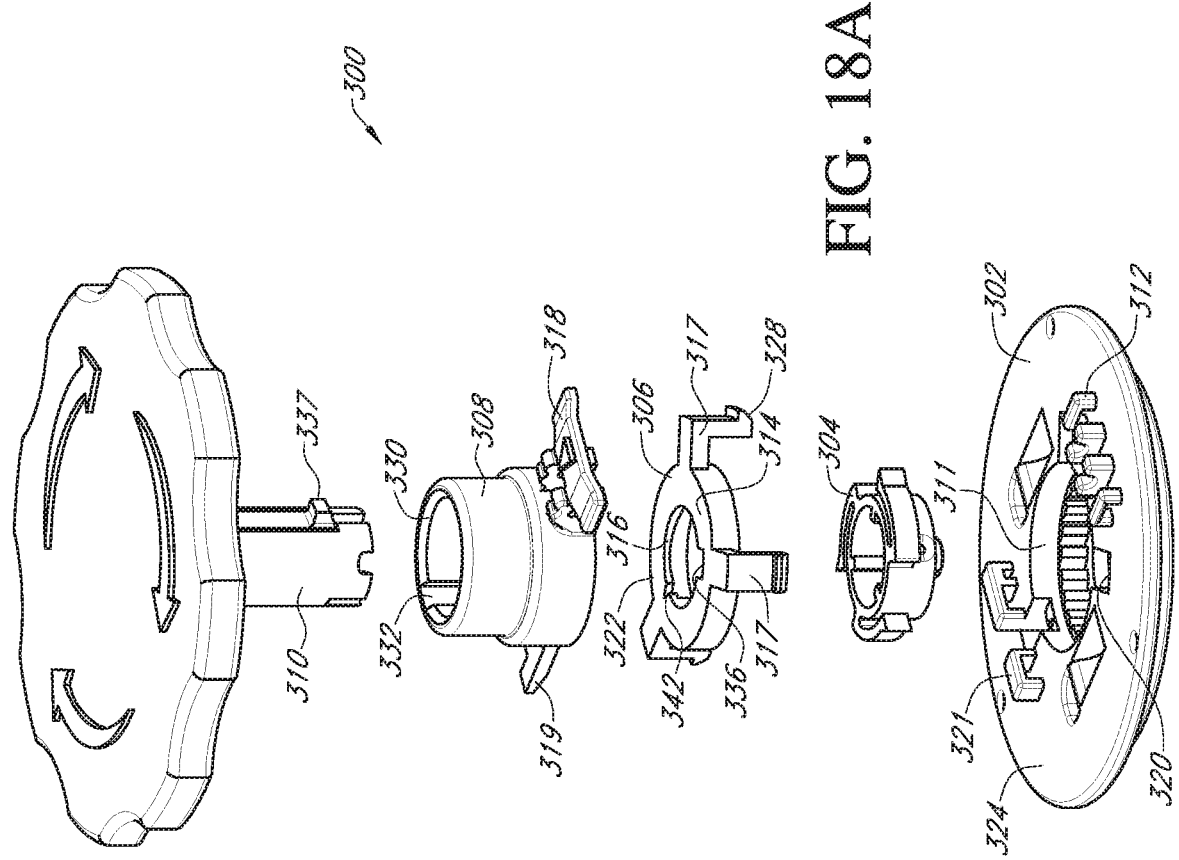
FIG. 18A shows an exploded perspective view of a valve holder for a prosthetic mitral valve according to a third embodiment of the invention.
Figure 18B:
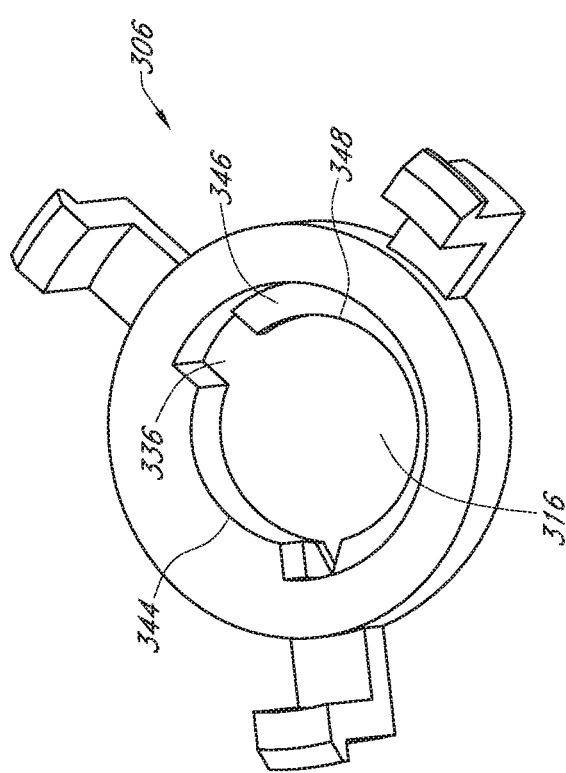
FIG. 18B shows a perspective view of an underside of a guide of the valve holder of FIG. 18A.
Figure 18C:
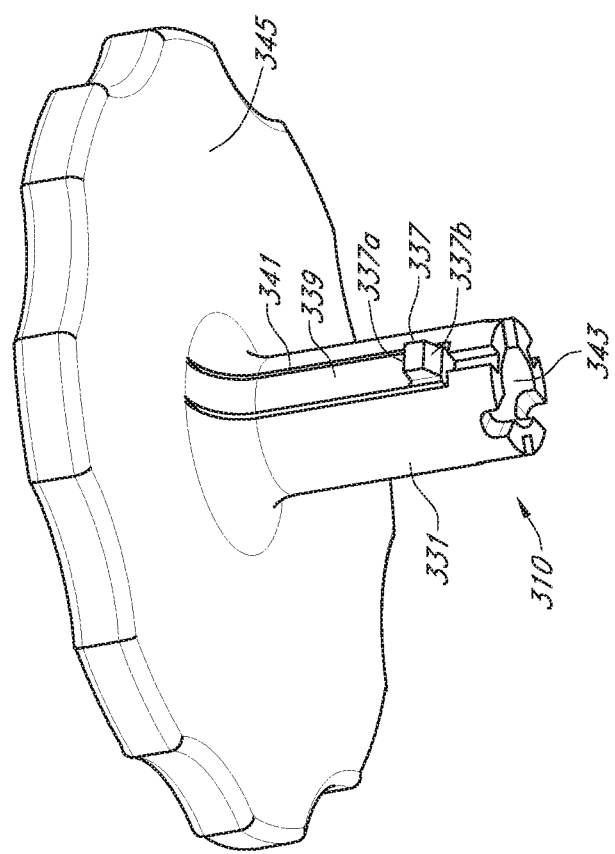
FIG. 18C shows a perspective view of an activator dial of the valve holder of FIG. 18A.
Figure 19:
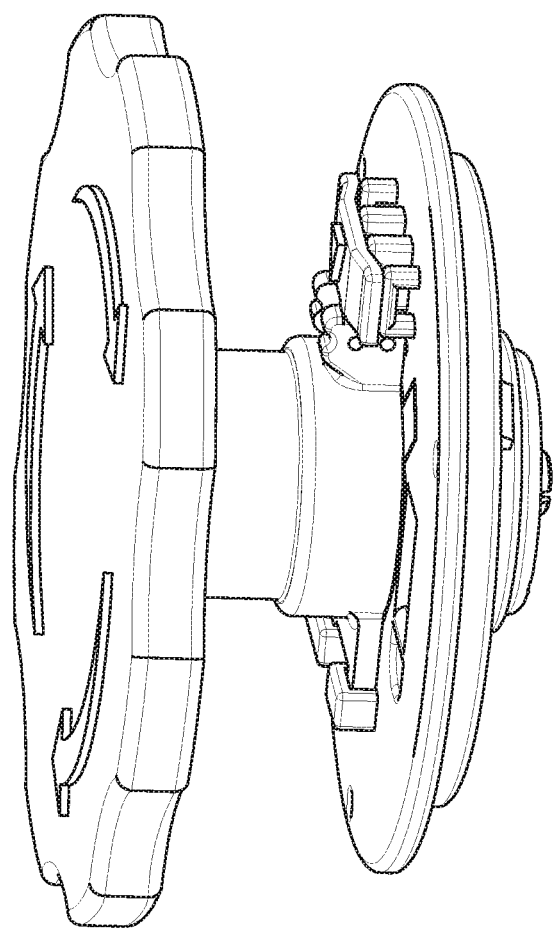
FIG. 19 shows a perspective view of the valve holder of FIG. 18A in an assembled state.
Figure 20:
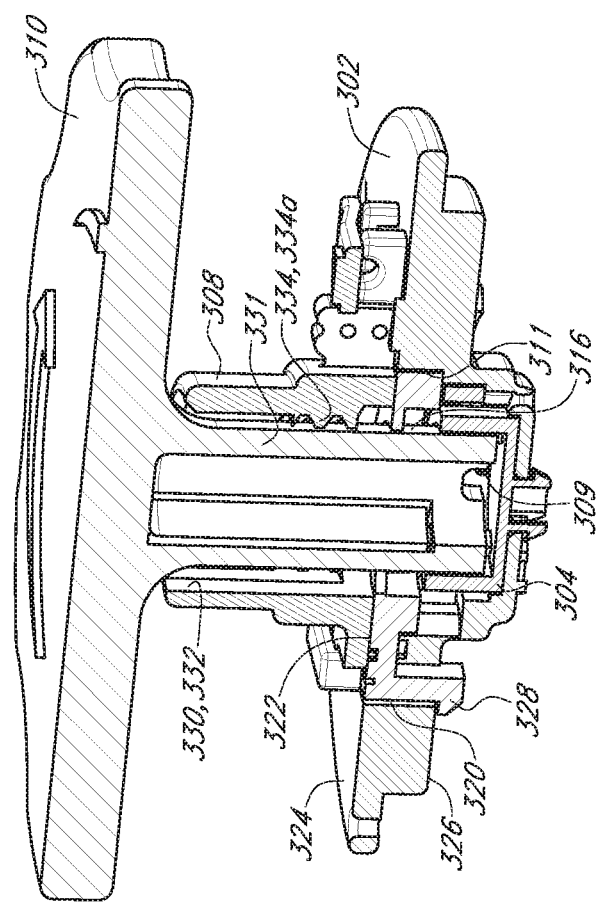
FIG. 20 shows a cross-sectional view of the valve holder of FIGS. 18A and 19.

FIGS. 18A to 20 show views of a valve holder 300 according to a third embodiment. FIG. 18A shows an exploded perspective view of the valve holder 300, FIG. 18B shows a perspective view of an underside of a guide 306 of the valve holder 300, FIG. 18C shows a perspective view of an activator dial 310 of the valve holder 300, FIG. 19 shows a perspective view of the valve holder 300 in an assembled state, and FIG. 20 shows a cross-sectional view of the valve holder 300 in the assembled state.

The valve holder 300 of the third embodiment allows the use of an inexpensive, reusable handle system, with a mitral valve holder that is activated or deployed to reduce or eliminate the occurrence of suture looping. As in the first and second embodiments, the valve holder 300 of the third embodiment includes integrated alignment features or other safety features, such that over-deployment or under-deployment of the valve holder 300 is prevented or avoided. The valve holder 300 of the third embodiment differs from the valve holders 100, 200 of the first and second embodiments, for example, in that the third embodiment removes the swiveling functions of the delivery mounts 106, 206 and delivery handles 108, 208 of the first and second embodiments. Instead, the valve holder 300 can be attached and implanted via an inexpensive, reusable handle. Thereby, the valve holder 300 of the third embodiment can require fewer components than the first and second embodiments, a simpler assembly of the valve holder 300, and may provide a lower cost system.

Figure 22:
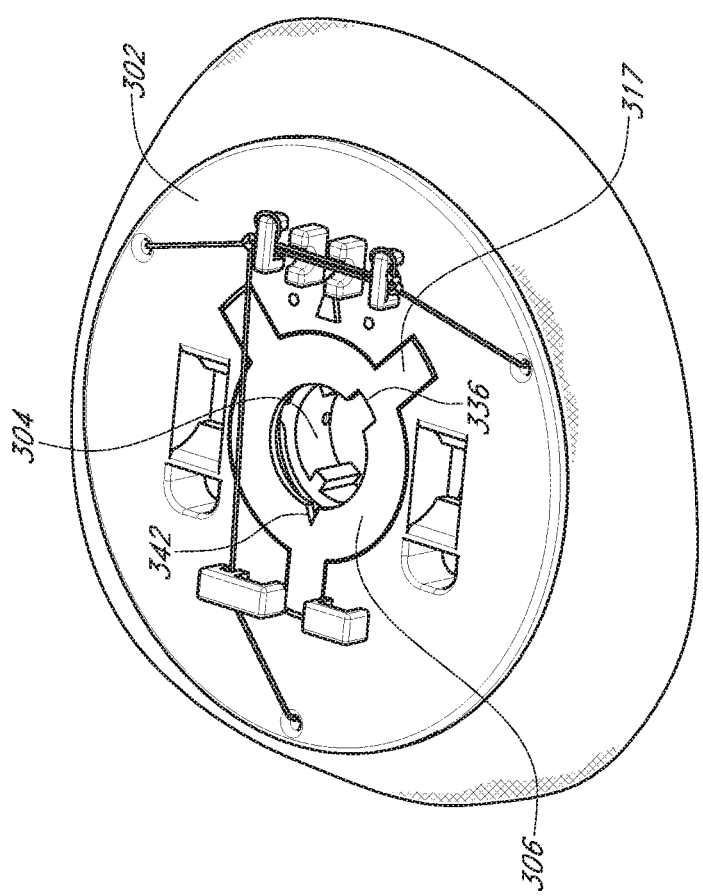
FIG. 22 shows a perspective view of the valve holder of FIGS. 18A to 21 in an assembled state with a latch removed.
Figure 23:
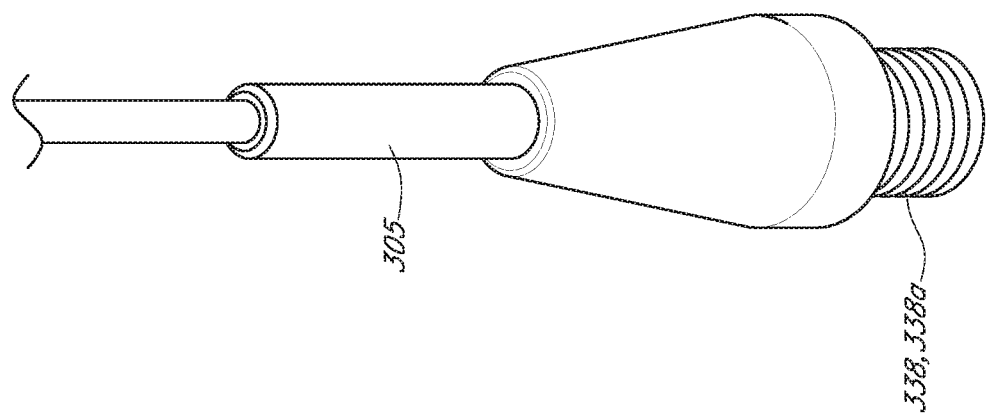
FIG. 23 shows a perspective view of a handle that can be used with the valve holder of FIGS. 18A to 22.
Figure 24:
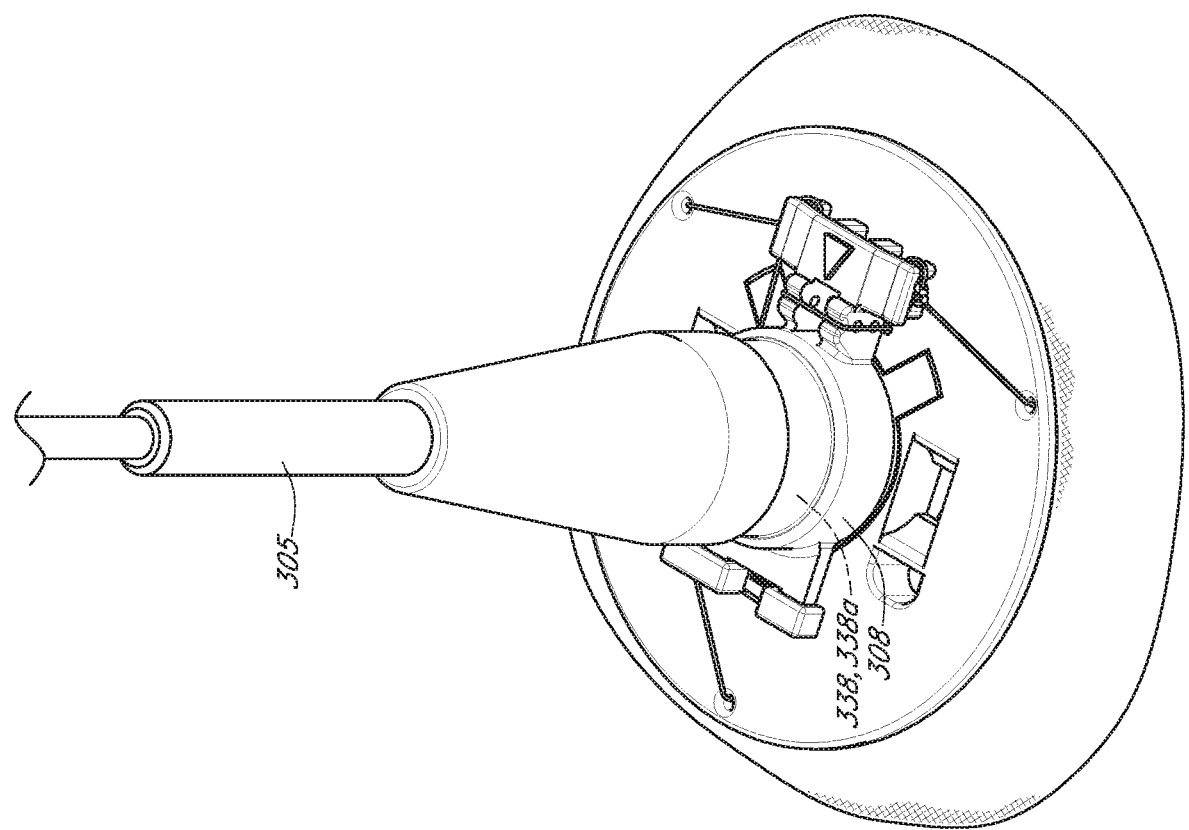
FIG. 24 shows a perspective view of the handle of FIG. 23 attached to the valve holder of FIGS. 18A to 22.

The valve holder 300 of the third embodiment includes a body 302, a rotor 304, a guide 306, a delivery latch 308, and an activator or activator dial 310. Similar to the first and second embodiments, a prosthetic heart valve can be attached to the body 302 of the valve holder 300 of the third embodiment (see FIGS. 21, 22, and 24). The rotor 304 is positioned in a bore of the body 302 and is adjustable using the dial 310 to deploy or activate the valve holder 300 for adjusting the prosthetic valve to a delivery position, as in the first and second embodiments. In the delivery position, the commissure posts of the prosthetic valve are urged downward and radially inwards toward a center of the valve to reduce or eliminate suture looping. As described in further detail below, the valve holder 300 includes an alignment keyway 336 for limiting rotation of the dial 310 and the rotor 304 relative to the body 302. This is to prevent over-deployment or under-deployment of the valve. The alignment keyway 336 is provided on a guide 306, which is attached to the body 302. Unlike the first and second embodiments, the third embodiment does not include a swiveling delivery mount coupled to a delivery handle. Instead, the delivery latch 308 is attached to the body 302, and is used to connect to a delivery handle 305 (see FIGS. 23 and 24).

The body 302 and rotor 304 of the third embodiment can be the same components or similar components as the body 202 and rotor 204 of the second embodiment. In particular, the body 302 and rotor 304 can be attached to the prosthetic valve using the same suture routing as described above with respect to the first and second embodiments. That is, three sutures can be used to attach the valve holder 300 to the commissure posts on the prosthetic valve as described above, and in some embodiments, a single suture line can be used to connect the prosthetic valve to the holder 300, also as described above. In addition, the body 302 includes a suture mount 312, which is the same or similar to the suture mount 212 of the second embodiment, and can provide a single access point to release the valve from the holder.

Meanwhile, the body 302, rotor 304, and dial 310 include the one-way ratcheting mechanism of the first and second embodiments to move the holder 300 into the deployed state by pulling the commissures of the prosthetic valve down and radially inward towards the center of the valve, and the description thereof will not be repeated, As described above with respect to the first and second embodiments, a central shaft or stem 331 of the dial 310 can be inserted into and connected to the rotor 304, such that turning the dial 310 rotates the rotor 304. Also as described above with respect to the first and second embodiments, holes in the rotor 304 (e.g., in sidewalls of the rotor 304) can provide attachment points for connecting and routing sutures. In some embodiments, the central shaft 331 is hollow and has an internal cavity (see FIG. 20), for example, to provide clearance for the sutures connected to inside of the rotor 304. The central shaft 331 can be inserted into the rotor 304 such that a bottom surface of the central shaft 331 is positioned adjacent or near a correspondence horizontal surface of the rotor 304. In such embodiments, a lower portion of the central shaft 331 can include openings (e.g., notches) 309 to aid with suture routing (see FIG. 20). The openings 309 can extend through the walls of the central shaft 331 and exposes the holes in the rotor 304 used to connect to the sutures.

Similar to the delivery mounts 106, 206 of the first and second embodiments, the guide 306 of the third embodiment provides ease of use and prevents misuse of the holder 300 during deployment. As shown in FIG. 20, the guide 306 is positioned above the rotor 304 such that the dial 310 must pass through a central opening 316 of the guide 306 before the dial 310 can be connected to the rotor 304. The guide 306 includes a keyway 336 and a wall 344, which provide alignment for the activator dial 310 via a key or protrusion 337 on the central shaft 331 of the dial 310 (see FIGS. 18A and 18C). The keyway 336 and the wall 344 of the guide 306 act as a stop that limits rotation of the dial 310 and the rotor 304 relative to body 302.

As shown in FIG. 18C., in some embodiments, the key 337 of the dial 310 may be positioned on a flexible arm 339 of the central shaft 331. The flexible arm 339 may be spaced apart from the remainder of the central shaft 331 by gaps 341 on either side of the flexible arm 339 such that the flexible arm 339 is movable (e.g., bendable) relative to the remainder of the central shaft 331. The flexible arm 339 may be bent inwards relative to the remainder of the central shaft 331 and towards a cavity 343 of the dial 310. The flexible arm 339 may be resilient such that the flexible arm 339 may be bent by the application of a force and return to its original shape when the force is removed. The flexible arm 339 may be connected to an upper portion 345 of the dial 310.

In some embodiments, the dial 310 may be used in conjunction with the guide 306 to place the valve holder 300 in a deployed configuration as follows. The central shaft 331 of the dial 310 may be inserted into the central opening 316 of the guide 306 in an orientation such that the key 337 of the dial 310 is aligned with (e.g., rotationally aligned with) a portion of the guide 306. In some embodiments, the key 337 may be rotationally aligned with a marker 342 of the guide 306. The key 337 of the dial 310 extends from dial 310 with a length that is greater than the diameter of the central opening 316 of the guide 306. As such, upon insertion of the central shaft 331 into the guide 306, a lower surface 337b of the key 337 will contact an upper surface 332 of the guide 306. Due to the flexibility of the flexible arm 339 of the dial 310, contact between the key 337 of the dial 310 and the upper surface 332 of the guide 306 causes the flexible arm 339 to bend inwards into the cavity 343 such that the key 337 may pass through the central opening of the guide 306. The lower surface 337b of the key 337 has an oblique or slanted shape (e.g., via a chamfer or fillet) relative to the upper surface 332 of the guide 306 to facilitate inward bending of the flexible arm 339 (see FIG. 18C). Once the key 337 passes the central opening 316 of the guide 306, the flexible arm 339 returns to its original (e.g., unbent) shape. An upper surface 337a of the key 337 has a flat shape that matches an underside surface 346 of the guide 306 to prevent or hinder the flexible arm 339 from bending once the key 337 passes the central opening 316 of the guide 306 (see FIG. 18C). This is to retain the dial 310 in the guide 306 and prevent inadvertent or unintended removal of the dial 310 before deployment of the valve holder 300 is complete.

Once the key 337 passes the central opening 316 of the guide 306 and the dial 310 is connected to the rotor 304, the dial 310 may be rotated to cause the rotor 304 to rotate and deploy the valve, similarly described above with respect to the previous embodiments. The rotor 304 has a one-way ratcheting mechanism such that the dial 310 may only be rotated in one direction (e.g., clockwise relative to the orientation shown in FIGS. 18A and 19), and the dial 310 is prevented from being rotating in an opposite direction. The underside of the guide 306 has a channel or groove 348 to facilitate rotation of the dial 310 relative to guide 306, which provides clearance for the key 337 of the dial 310 during rotation. The channel 348 has a shape that encompasses a partial circumference of the guide 306. That is, the channel 348 has a circumference that is less than 360 degrees such that the activator dial 310 is restricted to less than one full rotation in use. The guide 306 additional has a wall 344 to prevent over-deployment or over-tightening of the valve. The wall 334 acts as a stop against the key 337 to limit further rotation of the dial 310 when the key 337 is rotated in the channel 348. The wall 344 is adjacent the keyway 336 of the guide 306 such that when the dial 310 has been fully rotated in the channel 348, the dial 310 may be removed by removing the key 337 upwards through the keyway 336. The keyway 336 is sized to permit the key 337 of the dial 310 to fit therethrough. Upon removal of the dial 310, the valve holder 300 is in the fully deployed configuration. In addition, the keyway 336 and the one-way ratcheting mechanism prevent under-deployment of the valve. The dial 310 is prevented or hindered from being removed from the guide 306 until the key 337 is aligned with the keyway 336.

As shown in FIG. 20, the guide 306 is positioned in a bore 311 of the body 302, and is coaxial with a central axis of the body 302 and the rotor 304. In some embodiments, the guide 306 is positioned in the body 302 such that an upper surface 322 of the guide 306 is flush with or recessed relative to an upper surface 324 of the body 302. The guide 306 includes a generally circular-shaped central hub 314 with the central opening 316, and a plurality of arms 317 extending from the central hub 314. In some embodiments, the central hub 314 may have other shapes (e.g., triangular, square, rectangular, irregularly shaped, or otherwise shaped). As described above, the central opening 316 of the guide 306 is sized to permit the central shaft 331 of the activator dial to extend therethrough in order for the dial 310 to engage with the rotor 304 for deployment of the valve holder 300. In some embodiments, the guide 306 may include the marker 342 for identifying a connection orientation of the guide 306 relative to the body 302. The marker 342 may be aligned with one of the arms 317.

The arms 317 of the guide 306 are used to connect the guide 306 to the body 302. In the embodiment shown in FIG. 20, the guide 306 includes three arms 317, but can include more or fewer arms 317 in other embodiments. When three arms 317 are included in the guide 306, the arms 317 can extend from the guide 306 at approximately 120 degrees relative to each other. The body 302 includes a plurality of openings or channels 320 to connect the guide 306 to the body 302. The openings 320 of the body 302 can extend through the body 302 from the upper surface of the body 302 to a lower surface 326 of the body 302. The arms 317 of the guide 306 contain connection elements 328 that are designed to connect to the body 302 when the arms 317 are inserted into the openings 320 of the body 302. In some embodiments, the connection elements 328 of the guide 306 may include flat surfaces that mate with (e.g., abut) the lower surface 326 of the body 302. The arms 317 of the guide 306 may be resilient. In some embodiments, the arms 317 may connect to the body 302 via a snap fit, press fit, or other connection. In some embodiments, the guide 306 may be connected to the body 302 via a threaded engagement, and/or via pins or other fasteners or connection types.

The delivery latch 308 is positioned on the guide 306, as shown in FIG. 20, and is coaxial with the central axis of the body 302, the rotor 304, and the guide 306. In some embodiments, the delivery latch 308 is positioned on the upper surface 322 of the guide 306.

The delivery latch 308 includes a central opening 330 that extends therethrough. The central opening 330 is designed to receive the dial 310, which as described above, is used to deploy or activate the valve holder 300 to adjust the prosthetic valve to the delivery position. In particular, the delivery latch 308 enables the stem of 331 of the dial 310 to be inserted into the latch 308, inserted into the guide 306, and connected to the rotor 304 for deploying the valve holder 300. When the dial 310 is removed from the latch 308, the central opening 330 of the delivery latch 308 is designed to receive and connect to the delivery handle 305 for implantation of the prosthetic valve. However, while the dial 310 is positioned inside the delivery latch 308, the dial 310 prevents the handle 305 from being inserted into delivery latch 308. Thereby, the dial 310 acts as a feature that prevents implantation until the dial 310 has been removed from the valve holder 300. Safety of procedures using the valve holder 300 are thereby enhanced, helping to reduce or eliminate misuse of the holder 300 during operation.

Figure 21:
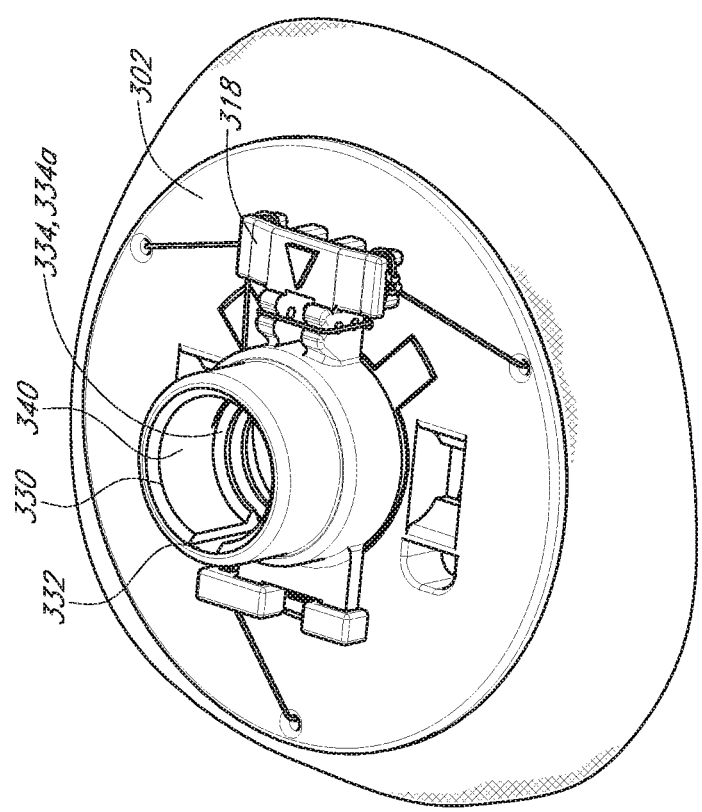
FIG. 21 shows a perspective view of the valve holder of FIGS. 18A to 20 in an assembled state with sutures.

The central opening 330 of the delivery latch 308 is sized to permit the stem 331 and key 337 of the dial 310 to be inserted into the opening 330 and pass through the latch 308, so that the stem 331 engages the ratchet mechanism of the body 302 and rotor 304, and so that the key 337 of the dial 310 engages the guide 306 as described above. In some embodiments, the central opening 330 includes a generally circular cross section. In some embodiments, the central opening 330 includes a generally circular cross section with a notch 332 for guiding the key 337 of the dial 310 through the delivery latch 308 at a particular rotational orientation, as shown in FIGS. 18, 20, and 21.

The central opening 330 of the delivery latch 308 includes an engagement portion 334 to mate with a corresponding engagement feature 338 of the handle 305. The handle 305 is configured to be inserted into the central opening 330 of the latch 308 and removably coupled to the latch 308 for implantation. In some embodiments, the engagement portion 334 of the latch 308 and the engagement feature 338 of the handle 305 include mating threads 334a, 338a. In such an embodiment, the opening 330 of the latch 308 can include a non-threaded lead-in portion 340 located adjacent the threads 334a. When the handle 305 is inserted into the central opening 330 of the latch 308, the threads 338a of the handle 305 may first reach the non-threaded portion 340 of the latch 308 before reaching the threads 334a of the latch 308. The non-threaded portion 340 helps prevent potential cross threading and particle generation by ensuring axial alignment of the threads 338a of the handle 305 and threads 334a of the latch 308. The threads 338a of the handle 305 are provided on an end or tip of the handle 305. In some embodiments, the threads 338a are made of a single piece and are crimped onto a nitinol shaft of the handle 305.

In some embodiments, an inner diameter between the threads 334a in the central opening 330 is sized such that the stem 331 and key 337 of the dial can pass therethrough. In embodiments containing the notch 332 in the central opening 330, the notch 332 can extend through the threads 334a of the latch 308 for guiding the key 337 of the dial 310 through the delivery latch 308. In such embodiments, the inner diameter between the threads 334a in the central opening 330 may be sized such that only the stem 331 of the dial 310 can pass through the threads, but not the key 337 (i.e., the key 337 fits through the notch 332 instead of the inner diameter between the threads 334a). This allows for a diameter of the stem 331 of the dial 310 to be smaller and the threads 338a of the handle 305 to be smaller. In some embodiments, the mating threads 334a, 338a have, for example, from a #10-24 thread to a 7/16"-14 thread, or an M4×0.7 thread to an M12×1.75 thread.

Meanwhile, the delivery latch 308 of the third embodiment includes a guard 318 that is the same or similar to the guard 218 of the delivery mount 206 of the second embodiment. The guard 318 is located at a periphery of the delivery latch 308. Opposite to the guard are protrusions 319 for engaging horizontal openings 321 on the body 302. The guard 318 and protrusions 319 are used to connect the delivery latch 308 to the body 302. The guard 318 allows a single suture to connect the delivery latch 308 to the body 302, as described above for the delivery mount 206. Further, the guard 318 provides an additional safety feature against inadvertent or premature release of the valve from the holder 300. When the delivery latch 308 is coupled to the holder 300, the guard 318 is aligned with the suture mount 312 of the body 302, and is positioned over and covers the suture mount 312, thereby preventing or reducing inadvertent or unintended cutting or breaking of the sutures connecting the holder 300 to the valve. When the delivery latch 308 is removed, the suture mount 312 is revealed and the suture or sutures connecting the valve holder 300 to the valve can then be cut or untied to release the valve.

Assembly of the holder 300 according to some embodiments is as follows. First, the rotor 304 is received in the body 302 similar to the second embodiment. Next, the guide 306 is coupled to the body 302 in position over the rotor 304. In particular, the arms 317 of the guide 306 are inserted into the openings 320 of the body 302. Next, one or more sutures are used to connect the holder 300 to the prosthetic valve, as described above with respect to the second embodiment. In some embodiments, the holder 300 may be connected to the prosthetic valve before the guide 306 is coupled to the body 302. Next the delivery latch 308 is coupled to the body 302 in position over the guide 306. The delivery latch 308 is coupled to the body 302 using one or more sutures, the guard 318, and the protrusions 319. When all of the described features are assembled, the valve holder 300 is in position to be deployed using the activator dial 310, similarly as discussed with respect to the first and second embodiments. In particular, the activator dial 310 is inserted into the central opening 330 of the latch 308, passed through the latch 308 and the guide 306, and connected to the rotor 304. The activator dial 308 is rotated to deploy the valve holder 300, and is then removed from the holder 300. Once the activator dial 310 is removed, the handle 305 can be inserted into and connected to the latch 308 for insertion and implantation of the attached valve into a patient. In other embodiments, the assembly sequence can be varied to achieve the same or similar assembled combinations.

Meanwhile, various different features from the different embodiments discussed above can also be combined into a single modified valve holder. In addition, various other modifications or alternative configurations can also be made to the valve holder according to the above described embodiments.

The presented embodiments also include an introducer which aids in delivering valve holders in minimally invasive surgical procedures. The introducer can be used with collapsible surgical valves to introduce the valves into a narrow surgical incision, such as a thoracotomy. The introducer can be used, for example, for delivering a prosthetic mitral valve to the mitral position. The introducer has a funnel-like shape for passing a collapsible heart valve from outside the body to inside the body through a narrow opening, such as the space between two ribs. In thoracotomy procedures, an incision is introduced into the chest cavity through the chest wall. In intercostal approaches, the incision is made between adjacent ribs to minimize cuts through bone, nerves, and muscle. In a typical thoracotomy procedure, the distance between the ribs, without spreading the ribs, is from about 15 mm to about 20 mm. Parallel to the ribs, the incision can be longer as needed, for example, approximately 45 mm or greater. Collapsible valve holders can have a small size that is particularly suited to fit in the small gap between the ribs in thoracotomy procedures.

Figure 25:
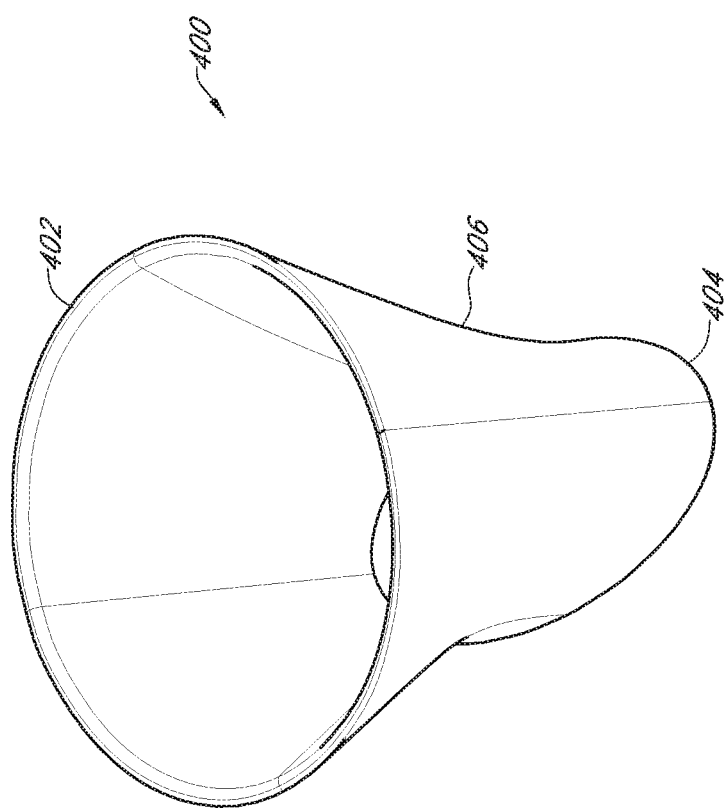
FIG. 25 shows a perspective view of an introducer for use with a valve holder.
Figure 26:
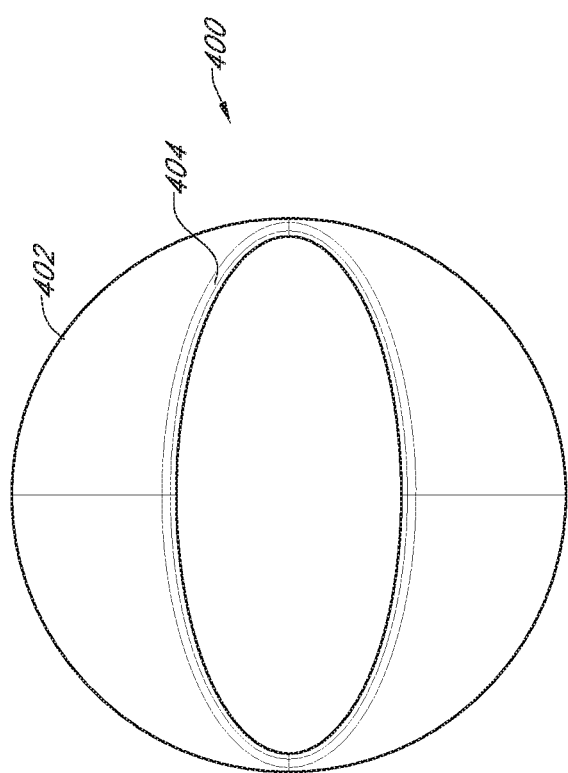
FIG. 26 shows a front view of the introducer of FIG. 25.

FIGS. 25 to 26 show views of an introducer 400 for introducing a valve and holder into a human body according to another embodiment. The introducer 400 provides a simple alternative approach for implanting collapsible heart valves connected to flexible holders through a minimal size incision, such as in a thoracotomy procedure. Due to the small gap between human ribs, the introducer 400 is used as an aid for inserting valves mounted on alternative flexible holders past the ribs and into the chest cavity during a thoracotomy or other minimally invasive procedures.

The introducer 400 has a hollow, funnel-like shape for receiving flexible holders with mounted valves, with a central axis of the valves pointed in a direction of insertion, for example, with an outflow end of the valve pointed or directed towards the introducer 400. The introducer 400 has a first, proximal end 402, and a second, distal end 404. The distal end 404 of the introducer faces towards the incision, while the proximal end 402 faces away from the incision and towards the operator of the holder. The proximal end 402 has a circular cross-sectional shape corresponding to the circular shape of the prosthetic heart valves. In use, the proximal end 402 is located outside of the incision. In one embodiment, the cross-section of the proximal end 402 is 45 mm in diameter. The distal end 404 has an oval cross-sectional shape corresponding to a size and shape of a surgical opening between ribs in a thoracotomy procedure. In one embodiment, the major diameter of the cross section of the distal end 404 is about 45 mm in diameter and the minor diameter of the cross section is from about 15 mm to about 20 mm in diameter. Between the proximal and distal ends 402, 404, the introducer 400 includes a smooth transition zone or region 406 connecting the ends 402, 404. The transition region 406 may have a smooth, continuous inner profile between the ends 402, 404, which is substantially free from corners.

The introducer 400 can be made very inexpensively as a disposable item that is supplied with a valve. For example, the introducer 400 can be made of or include polypropylene, or any other suitable material having a low coefficient of friction. The introducer 400 can be a molded part. Meanwhile, the valve to be implanted can be made of a Nitinol wireform band exhibiting a large degree of elasticity. In one embodiment, the valve exhibits superelastic properties.

In use, the introducer 400 is first introduced into an incision in the chest cavity with the distal end 404 positioned between two ribs. The valve, connected to a flexible holder, is inserted into the proximal end 402 of the introducer 400. The valve is then pushed towards the smaller, distal end 404 of the introducer 400, where the valve elastically deforms to squeeze through the smaller cross-sectional shape. The valve can take on the oval shape of the introducer or another generally collapsed shape as it is pushed through. Once the valve clears the distal end 404 of the introducer 400, the valve regains its undeformed shape (e.g., a circular shape). In this way, the deformation of the valve and holder is passive, being imposed or dictated by the shape of the introducer rather than by a mechanism on the holder itself. The advantage of this configuration is that the holder can be a very inexpensive molded component.

In one embodiment, a length of the introducer 400 is sufficient to introduce the valve into an internal surface of the chest wall past the rib cage. In such an embodiment, a length of the introducer from the proximal end 402 to the distal end 404 may be up to about 40 mm long. In other embodiments, a length of the introducer can be made longer. In one embodiment, the distal end 404 could be extended many more centimeters so that it would extend, for example, into the left atrium of the heart, for a mitral valve replacement, to act as an atrial retractor. Meanwhile, the proximal end 402 of the introducer 400 can remain positioned outside of the incision in the chest cavity. This would provide a tunnel from the outside of the body all the way to the site of implantation at the annulus.

In alternative embodiments, the introducer 400 can include various additional features, for example, a slit in a wall of the introducer 400 can be provided to give clearance for sutures passing through a side of the introducer during surgical procedures. In addition, lighting, such as light emitting diodes ("LEDs") and/or at least one optical fiber, can be added to the introducer, along with a power supply, such as batteries, to power the lighting. LED lighting can be inexpensively added to the introducer with a built-in battery. The lighting can be particularly useful with the extended version of the introducer. The lighting can provide excellent illumination at the site of implantation and reduce the need for additional external lighting.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A valve holder for holding and implanting a prosthetic heart valve comprising a frame and a plurality of flexible leaflets, the valve holder comprising:
   a body for holding the prosthetic heart valve, the body having a top surface, a bottom surface, and a central axis extending between the top and bottom surfaces;
   a rotor positioned in the body, wherein when the prosthetic heart valve is coupled to the body, the rotor is rotatable around the central axis of the body to adjust the prosthetic heart valve to a delivery position; and
   a latch having an opening couplable with a handle, and through which an activator is couplable to the rotor for rotating the rotor around the central axis of the body; further comprising the handle, wherein the opening of the latch comprises a threaded portion matable with a threaded portion of the handle.

2. The valve holder of claim 1, wherein the threaded portion of the handle is at a tip of the handle.

3. The valve holder of claim 2, wherein the opening of the latch comprises an unthreaded portion followed by the threaded portion such that when the handle is inserted into the latch, the tip passes through the unthreaded portion before passing into the threaded portion.

4. The valve holder of claim 1, wherein the rotor comprises an opening configured to receive the activator, and wherein the opening in the rotor and the opening in the latch are coaxial with the central axis of the body.

5. The valve holder of claim 4, further comprising the activator, wherein the activator is separable from and connectable to the rotor for rotating the rotor around the central axis of the body.

6. The valve holder of claim 5, further comprising a guide coupled to the body for facilitating coupling of the activator to the rotor when the activator is at a first rotational orientation relative to the rotor.

7. The valve holder of claim 6, wherein the guide further facilitates decoupling of the activator from the rotor when the activator is at a second rotational orientation different from the first rotational orientation relative to the rotor.

8. The valve holder of claim 7, wherein the activator is limited to rotating the rotor less than one full turn around the central axis of the body between the first rotational orientation and the second rotational orientation.

9. The valve holder of claim 7, wherein when the activator is coupled to the rotor at the second rotational orientation, the rotor is restricted from rotating in either rotational direction.

10. The valve holder of claim 6, wherein the guide is positioned between the latch and the rotor, and wherein the guide defines an opening to permit the activator to access the rotor.

11. The valve holder of claim 5, wherein the opening of the latch comprises an engagement portion configured to engage the handle, and wherein the activator is connectable to the rotor without engaging the engagement portion of the latch.

12. The valve holder of claim 1, further comprising the handle and the activator, wherein when the handle is received in the opening in the latch, the handle blocks the activator from being connected to the rotor.

13. The valve holder of claim 1, further comprising the handle and the activator, wherein the activator is connectable to the rotor for rotating the rotor around the central axis of the body.

14. A system comprising:
the valve holder of claim 1;
the prosthetic heart valve; and
the activator, wherein the activator is connectable to the rotor at the top surface of the body and wherein the prosthetic heart valve is connectable to the bottom surface of the body.

15. A system comprising:
the valve holder of claim 1;
the prosthetic heart valve; and
the handle, wherein when the prosthetic heart valve is connected to the bottom surface of the body and the handle is connected to the latch, the top surface of the body faces the handle.

16. The valve holder of claim 1, wherein the rotor is rotatable relative to the latch.

17. The valve holder of claim 1, wherein the opening of the latch comprises an engagement portion configured to engage the handle.

18. The valve holder of claim 17, wherein the engagement portion comprises a thread.

19. The valve holder of claim 1, wherein the rotor is rotatable around the central axis of the body in a first direction and not rotatable in a second direction opposite the first direction.

* * * * *